United States Patent
Miller et al.

(10) Patent No.: US 11,547,432 B2
(45) Date of Patent: Jan. 10, 2023

(54) ULTRASONIC SURGICAL INSTRUMENT WITH PRE-ASSEMBLED ACOUSTIC ASSEMBLY

(71) Applicant: Ethicon LLC, Guaynabo, PR (US)

(72) Inventors: Matthew C. Miller, Cincinnati, OH (US); Sean P. Conlon, Loveland, OH (US); Michael E. Boehm, Cincinnati, OH (US); Richard W. Flaker, Fairfield, OH (US); Bryce Hansen, Cincinnati, OH (US); Rafael J. Ruiz Ortiz, Mason, OH (US)

(73) Assignee: Cilag GmbH International, Zug (CH)

( * ) Notice: Subject to any disclaimer, the term of this patent is extended or adjusted under 35 U.S.C. 154(b) by 294 days.

(21) Appl. No.: 16/919,292

(22) Filed: Jul. 2, 2020

(65) Prior Publication Data
US 2020/0375626 A1    Dec. 3, 2020

Related U.S. Application Data

(63) Continuation of application No. 15/690,468, filed on Aug. 30, 2017, now Pat. No. 10,743,903.

(51) Int. Cl.
*A61B 17/32* (2006.01)
*A61B 17/00* (2006.01)
*A61B 17/29* (2006.01)

(52) U.S. Cl.
CPC ......... *A61B 17/320092* (2013.01); *A61B 17/320068* (2013.01); *A61B 2017/00455* (2013.01);
(Continued)

(58) Field of Classification Search
CPC .... A61B 17/320068; A61B 17/320092; A61B 2017/320094; A61B 2017/320071;
(Continued)

(56) References Cited

U.S. PATENT DOCUMENTS

| | | | |
|---|---|---|---|
| 5,322,055 A | 6/1994 | Davison et al. | |
| 5,792,135 A | 8/1998 | Madhani et al. | |

(Continued)

FOREIGN PATENT DOCUMENTS

| | | |
|---|---|---|
| WO | WO 2017/066087 A1 | 4/2017 |
| WO | WO 2017/100412 A1 | 6/2017 |

OTHER PUBLICATIONS

International Search Report and Written Opinion dated Nov. 22, 2018, for International Application No. PCT/IB2018/056326, 10 pages.

*Primary Examiner* — Tuan V Nguyen
(74) *Attorney, Agent, or Firm* — Frost Brown Todd LLC

(57) ABSTRACT

An ultrasonic surgical instrument includes a body, an ultrasonic supported by the body, a shaft extending distally from the body and defining a shaft axis, a waveguide extending distally through the shaft, and an end effector arranged at a distal end of the shaft. The end effector includes an ultrasonic blade coupled to a distal end of the waveguide and having a primary blade treatment surface configured to treat tissue, and a clamp arm coupled to the distal end of the shaft. The shaft and the waveguide are selectively rotatable relative to one another about the shaft axis through a predefined range of angular motion between an assembly state and an operational state. In the assembly state, the clamp arm and the primary blade treatment surface are rotationally offset from one another. In the operational state, the clamp arm and the primary blade treatment surface are rotationally aligned.

20 Claims, 23 Drawing Sheets

(52) U.S. Cl.
CPC ............... *A61B 2017/00477* (2013.01); *A61B 2017/2929* (2013.01); *A61B 2017/2933* (2013.01); *A61B 2017/2945* (2013.01); *A61B 2017/320071* (2017.08); *A61B 2017/320094* (2017.08)

(58) Field of Classification Search
CPC .......... A61B 2017/00455; A61B 2017/00477; A61B 2017/2929; A61B 2017/2933; A61B 2017/2945
See application file for complete search history.

(56) References Cited

U.S. PATENT DOCUMENTS

| | | | |
|---|---|---|---|
| 5,817,084 A | 10/1998 | Jensen | |
| 5,873,873 A | 2/1999 | Smith et al. | |
| 5,878,193 A | 3/1999 | Wang et al. | |
| 5,980,510 A | 11/1999 | Tsonton et al. | |
| 6,231,565 B1 | 5/2001 | Tovey et al. | |
| 6,283,981 B1 | 9/2001 | Beaupre | |
| 6,309,400 B2 | 10/2001 | Beaupre | |
| 6,325,811 B1 | 12/2001 | Messerly | |
| 6,364,888 B1 | 4/2002 | Niemeyer et al. | |
| 6,423,082 B1 | 7/2002 | Houser et al. | |
| 6,773,444 B2 | 8/2004 | Messerly | |
| 6,783,524 B2 | 8/2004 | Anderson et al. | |
| 7,524,320 B2 | 4/2009 | Tierney et al. | |
| 7,691,098 B2 | 4/2010 | Wallace et al. | |
| 7,806,891 B2 | 10/2010 | Nowlin et al. | |
| 8,057,498 B2 | 11/2011 | Robertson | |
| 8,461,744 B2 | 6/2013 | Wiener et al. | |
| 8,479,969 B2 | 7/2013 | Shelton, IV | |
| 8,573,461 B2 | 11/2013 | Shelton, IV et al. | |
| 8,573,465 B2 | 11/2013 | Shelton, IV | |
| 8,591,536 B2 | 11/2013 | Robertson | |
| 8,602,288 B2 | 12/2013 | Shelton, IV et al. | |
| 8,616,431 B2 | 12/2013 | Timm et al. | |
| 8,623,027 B2 | 1/2014 | Price et al. | |
| 8,663,220 B2 | 3/2014 | Wiener et al. | |
| 8,783,541 B2 | 7/2014 | Shelton, IV et al. | |
| 8,800,838 B2 | 8/2014 | Shelton, IV | |
| 8,820,605 B2 | 9/2014 | Shelton, IV | |
| 8,844,789 B2 | 9/2014 | Shelton, IV et al. | |
| 9,095,367 B2 | 8/2015 | Olson et al. | |
| 9,301,759 B2 | 4/2016 | Spivey et al. | |
| 10,743,903 B2 | 8/2020 | Miller et al. | |
| 2005/0216045 A1 | 9/2005 | Young et al. | |
| 2006/0241532 A1* | 10/2006 | Murakami | A61B 17/320092 601/2 |
| 2015/0141981 A1 | 5/2015 | Price et al. | |
| 2015/0164531 A1 | 6/2015 | Faller et al. | |
| 2016/0015419 A1 | 1/2016 | Hibner et al. | |
| 2016/0022305 A1 | 1/2016 | Lamping et al. | |
| 2016/0302820 A1 | 10/2016 | Hibner et al. | |
| 2017/0000541 A1 | 1/2017 | Yates et al. | |

\* cited by examiner

ULTRASONIC SURGICAL INSTRUMENT WITH PRE-ASSEMBLED ACOUSTIC ASSEMBLY

This application is a continuation of U.S. patent application Ser. No. 15/690,468, entitled "Ultrasonic Surgical Instrument with Pre-Assembled Acoustic Assembly," filed Aug. 30, 2017, issued as U.S. Pat. No. 10,743,903 on Aug. 18, 2020.

BACKGROUND

Ultrasonic surgical instruments utilize ultrasonic energy for both precise cutting and controlled coagulation of tissue. The ultrasonic energy cuts and coagulates by vibrating a blade in contact with the tissue. Vibrating at frequencies of approximately 50 kilohertz (kHz), for example, the ultrasonic blade denatures protein in the tissue to form a sticky coagulum. Pressure exerted on the tissue with the blade surface collapses blood vessels and allows the coagulum to form a hemostatic seal. The precision of cutting and coagulation may be controlled by the surgeon's technique and adjusting the power level, blade edge, tissue traction, and blade pressure, for example.

Examples of ultrasonic surgical devices include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; U.S. Pat. No. 8,623,027, entitled "Ergonomic Surgical Instruments," issued Jan. 7, 2014, the disclosure of which is incorporated by reference herein; U.S. Pat. No. 9,095,367, entitled "Flexible Harmonic Waveguides/Blades for Surgical Instruments," issued Aug. 4, 2015, the disclosure of which is incorporated by reference herein; and U.S. Pub. No. 2016/0022305, entitled "Ultrasonic Blade Overmold," published Jan. 28, 2016, issued as U.S. Pat. No. 9,750,521 on Sep. 5, 2017 the disclosure of which is incorporated by reference herein.

While various types of ultrasonic surgical instruments have been made and used, it is believed that no one prior to the inventor(s) has made or used the invention described herein.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
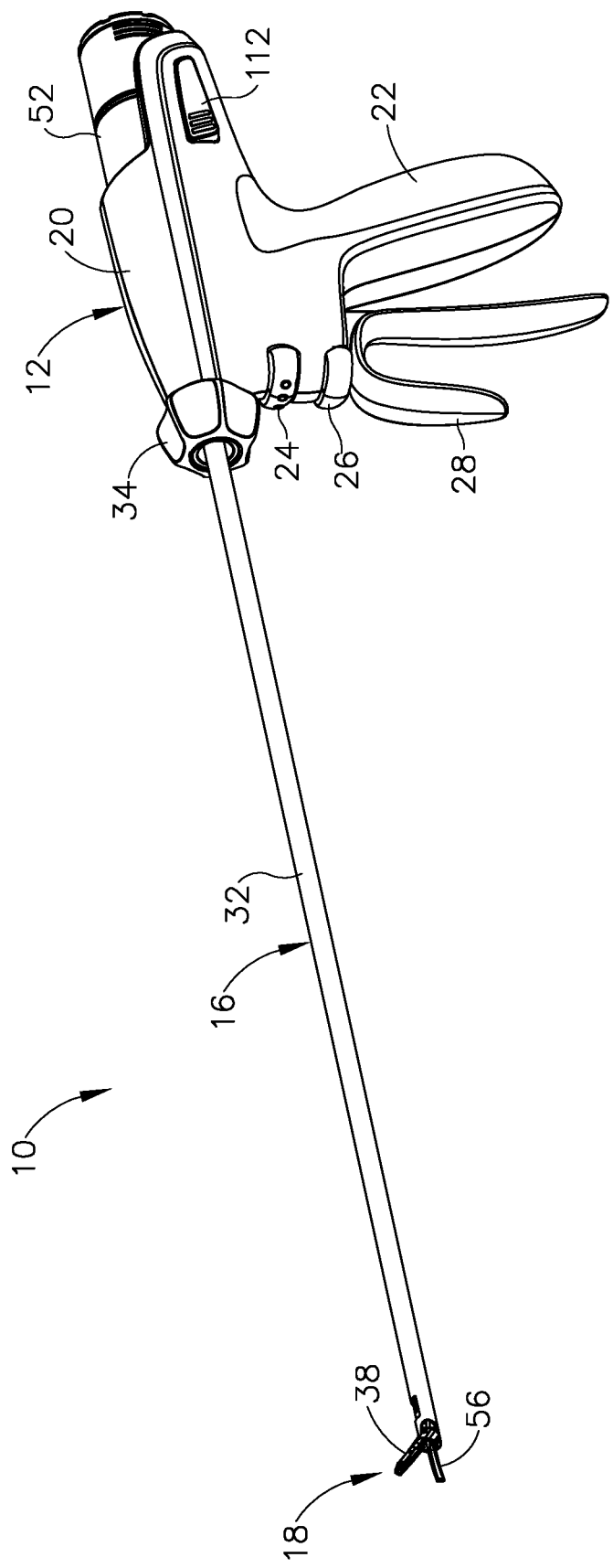
FIG. 1 depicts a perspective view of an exemplary ultrasonic surgical instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

I. Exemplary Ultrasonic Surgical Instrument Having Removable Acoustic Assembly

A. Overview of Exemplary Ultrasonic Surgical Instrument

Figure 2:
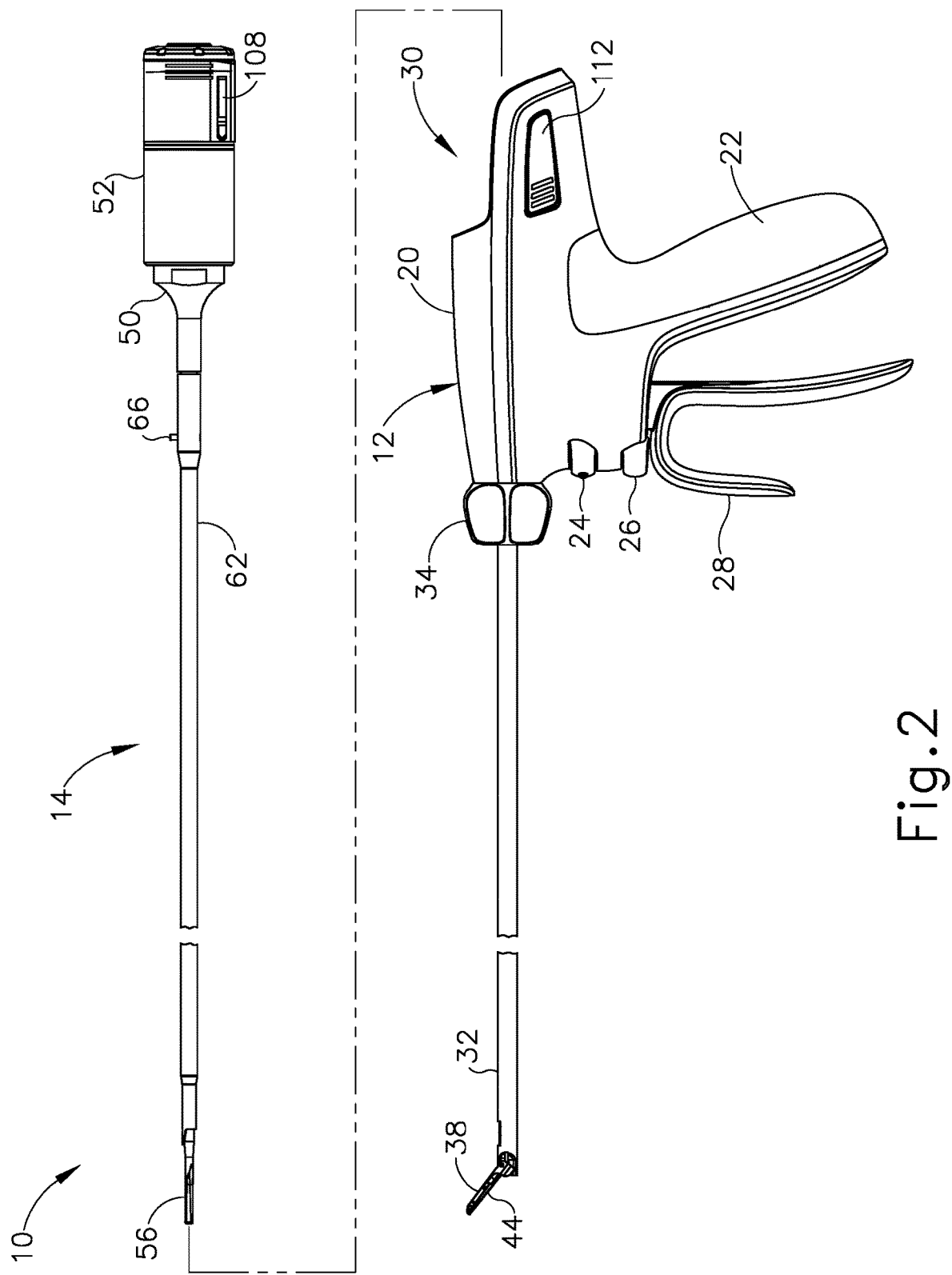
FIG. 2 depicts a side disassembled view of the ultrasonic surgical instrument of FIG. 1, having a handle assembly and a removable assembly.

FIGS. 1 and 2 show an exemplary ultrasonic surgical instrument (10) that includes a handle assembly (12) and a removable acoustic assembly (14) configured to selectively couple with and decouple from handle assembly (12). In the assembled state shown in FIG. 1, surgical instrument (10) presents a shaft assembly (16) extending distally from handle assembly (12), and an end effector (18) arranged at a distal end of shaft assembly (16). Handle assembly (12) comprises a body (20) including a pistol grip (22) and energy control buttons (24, 26) configured to be manipulated by a surgeon to control various aspects of ultrasonic energy delivered by surgical instrument (10). A trigger (28) is pivotably coupled to a lower portion of body (20) and is pivotable toward and away from pistol grip (20) to selectively actuate end effector (18). As shown in FIG. 2, body (20) includes a proximal body opening (30) configured to receive removable acoustic assembly (14), as described in greater detail below.

Figure 3:
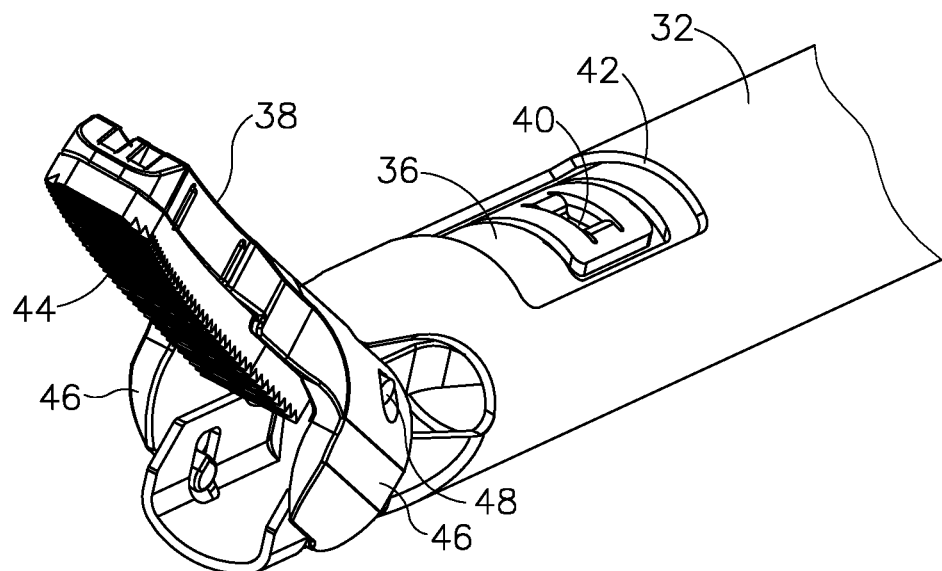
FIG. 3 depicts a perspective view of an outer shaft tube, a connector tube, and a clamp arm of the ultrasonic surgical instrument of FIG. 1.
Figure 4:
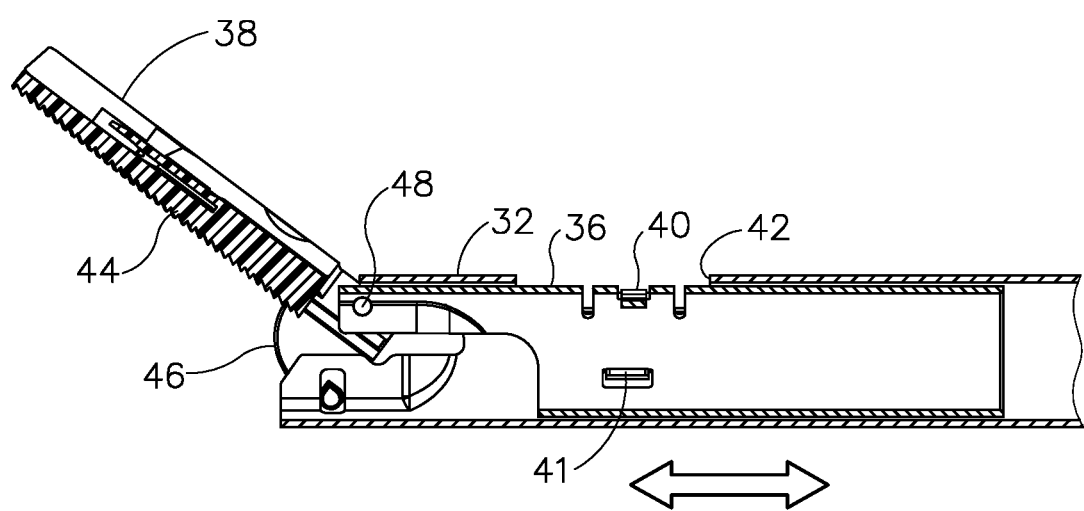
FIG. 4 depicts a side cross-sectional view of the outer shaft tube, connector tube, and clamp arm of FIG. 3.

An outer shaft tube (32) of shaft assembly (16) extends distally from handle assembly (12) and is movably coupled with body (20) such that outer shaft tube (32) is configured to translate relative to body (20), and rotate relative to body (20) with a rotation knob (34). As shown in FIGS. 3 and 4, a distal end of outer shaft tube (32) houses a connector tube (36) slidably disposed therein, and couples to a clamp arm (38). Connector tube (36) includes a snap arm (40) arranged on an upper side thereof, and is exposed through an upper longitudinal slot (42) formed in the distal end of outer shaft tube (32). Snap arm (40) is configured to couple to a distal end of an inner shaft tube (62) of shaft assembly (16) with a snap-fit connection, and thereby couple connector tube (36) with inner shaft tube (62) axially and rotationally, as described below. Connector tube (36) further includes a tab (41) that projects radially inwardly from a sidewall of connector tube (36). Tab (41) is configured to abut a distal edge of inner shaft tube (62) and thereby further ground connector tube (36) in a proximal direction relative to inner shaft tube (62) to facilitate closure of clamp arm (38), as described in greater detail below.

Clamp arm (38) includes a clamp pad (44) configured to engage and clamp tissue against an ultrasonic blade (56) of end effector (18) when clamp arm (38) is in a closed position. Clamp arm (38) further includes a pair of proximally extending clevis arms (46) that receive therebetween and pivotably couple to a distal end of connector tube (36) with a pivot pin (48) received through upper ends of clevis arms (46). Lower ends of clevis arms (46) include inwardly extending protrusions that pivotably couple with the distal end of outer shaft tube (32). Clamp arm (38) is configured to selectively pivot about pivot pin (48) toward and away from ultrasonic blade (56) upon actuation of outer shaft tube (32) relative to body (20) by trigger (28). In particular, clamp arm (38) is operatively coupled with trigger (24) by outer shaft tube (32) such that pivoting of trigger (24) toward pistol grip (20) drives proximal translation of outer shaft tube (32) relative to connector tube (36), and resultant pivoting of clamp arm (38) toward ultrasonic blade (56) to a closed position (not shown). Conversely, pivoting of trigger (28) away from pistol grip (22) drives distal translation of outer shaft tube (32) relative to connector tube (36), and resultant pivoting of clamp arm (38) away from ultrasonic blade (56) to an open position, shown in FIGS. 1-4. Structural components of handle assembly (12) that operatively couple trigger (28) with outer shaft tube (32) are described in greater detail below.

B. Removable Acoustic Assembly Having Alignment Pin

Figure 5:
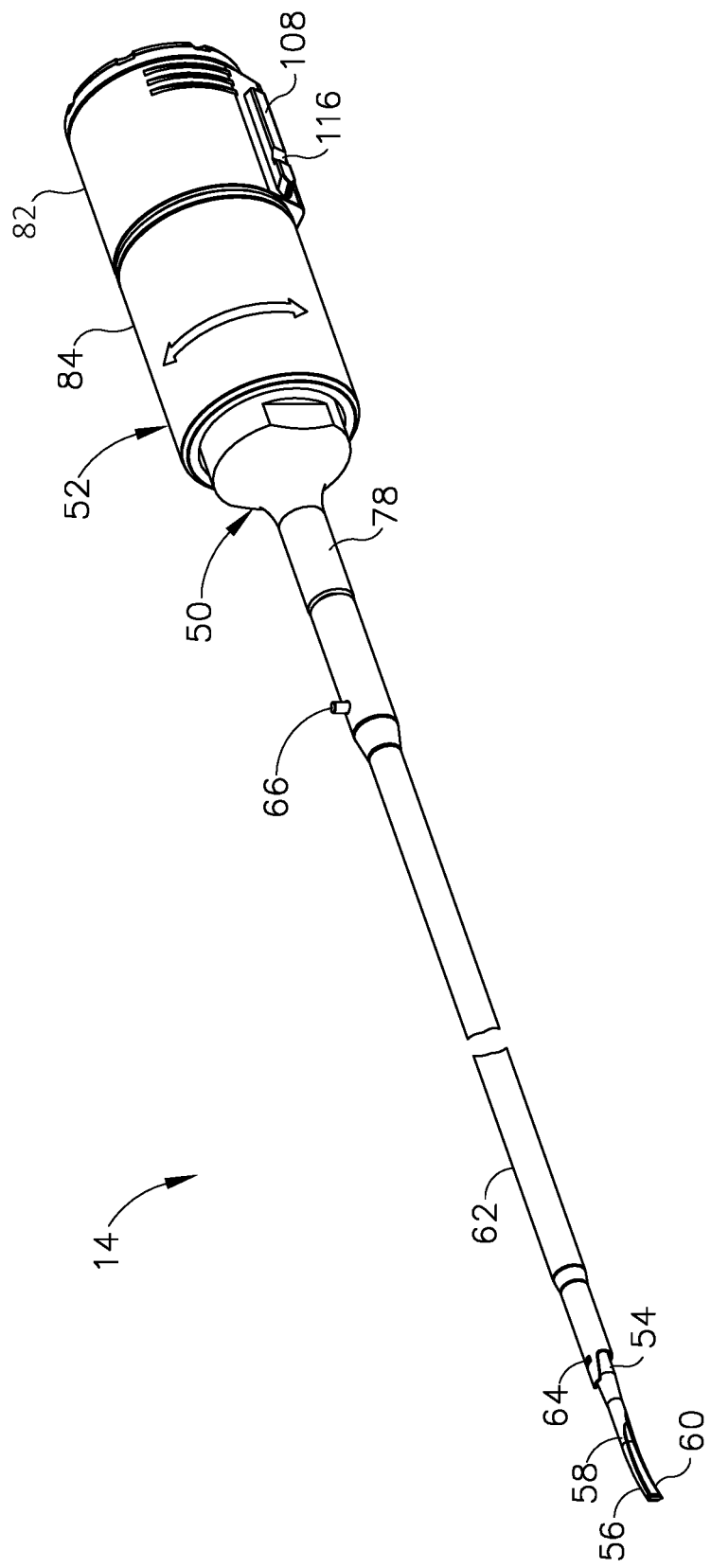
FIG. 5 depicts a perspective view of the removable assembly of FIG. 2.

As shown in FIGS. 2 and 5, removable acoustic assembly (14) generally includes an ultrasonic transducer (50), a transducer housing (52) encasing transducer (50), an ultrasonic waveguide (54) acoustically coupled to and extending distally from a distal end of transducer (50), and an ultrasonic blade (56) formed integrally with and extending distally from a distal end of waveguide (54). Transducer (50) is configured to drive (i.e., vibrate) waveguide (54) and blade (56) at ultrasonic frequencies for cutting and/or sealing tissue positioned in contact with blade (56). In the present example, ultrasonic blade (56) extends distally with a lateral curvature. Blade (56) includes a primary blade treatment surface (58) arranged on an upper side of blade (56), and a cutting edge (60) arranged on an opposing lower side of blade (56). Primary blade treatment surface (58) is configured to cut and/or seal tissue positioned (e.g., clamped) between blade (56) and clamp arm (38), and lower edge (60) is configured to cut tissue during "back-cutting" procedures.

Removable acoustic assembly (14) further includes an inner shaft tube (62) of shaft assembly (16). Inner shaft tube (62) houses waveguide (54) and extends distally from a distal end of transducer (50) to a distal end of waveguide (54). Waveguide (54) may be supported within inner shaft tube (62) by a plurality of nodal support elements (not shown) positioned at various locations along a length of waveguide (54) corresponding to acoustic nodes. As shown in FIG. 5, an upper side of a distal end of inner shaft tube (62) includes an opening (64) configured to receive snap arm (40) of connector tube (36) to facilitate coupling of inner shaft tube (62) with outer shaft tube (32), as described below.

An alignment pin (66) extends transversely through waveguide (54) and inner shaft tube (62) at a longitudinal location corresponding to a proximal acoustic node of waveguide (54), thereby coupling waveguide (54) and inner shaft tube (62) together axially and rotationally. An exposed end of alignment pin (66) protrudes radially outwardly from the upper side of inner shaft tube (62) at a position in angular alignment with distal opening (64) of inner shaft tube (62) and primary blade treatment surface (58) of ultrasonic blade (56). As described in greater detail below, the exposed end of alignment pin (66) is configured to engage alignment features disposed in the interior of handle assembly (12) to thereby guide rotation of waveguide (54), blade (56), and inner shaft tube (62) through a predefined range of angular motion relative to outer shaft tube (32) and clamp arm (38).

Figure 6:
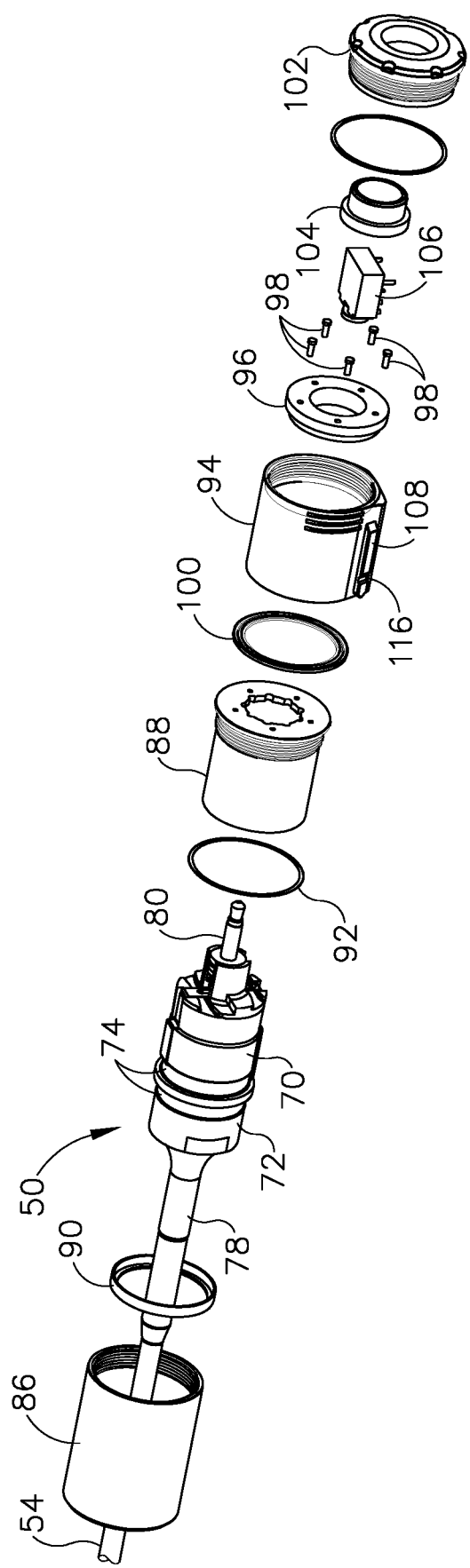
FIG. 6 depicts a disassembled perspective view of the removable assembly of FIG. 2.
Figure 7:
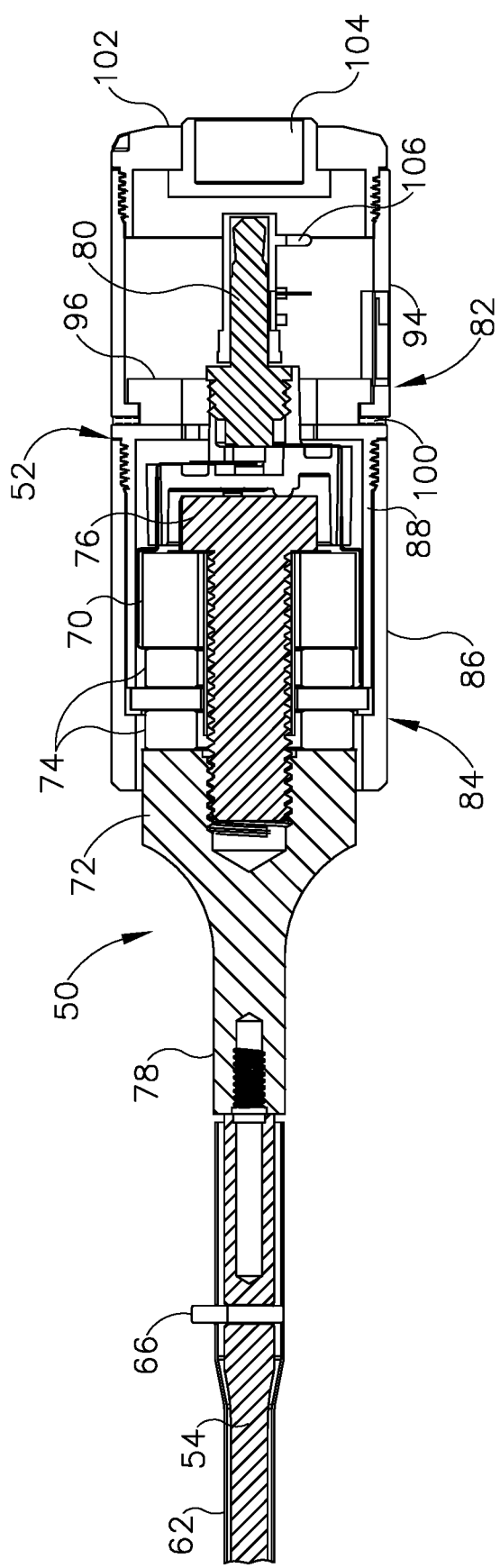
FIG. 7 depicts a side cross-sectional view of the removable assembly of FIG. 2.

FIGS. 5-7 show additional detail of removable acoustic assembly (14), including ultrasonic transducer (50) and transducer housing (52). Ultrasonic transducer (50) of the present example generally includes a first resonator (or "end-bell") (70), a conically shaped second resonator (or "fore-bell") (72), and a transduction portion arranged between end-bell (70) and fore-bell (72) and comprising a plurality of piezoelectric elements (74). A compression bolt (76) extends distally, coaxially through end-bell (70) and piezoelectric elements (74), and is threadedly received within a proximal end of fore-bell (72). A velocity transformer (or "horn") (78) extends distally from fore-bell (72) and couples with a proximal end of ultrasonic waveguide (50), for example via a threaded connection as shown in FIG. 7. An electrical post (80) extends proximally from end-bell (70) and electrically couples with piezoelectrical elements (74). In exemplary versions, ultrasonic transducer (34) may be further configured in accordance with any of the transducer configurations disclosed in the references incorporated by reference herein.

In use, a generator (not shown) is electrically coupled with ultrasonic transducer (50) and powers ultrasonic transducer (50) to produce ultrasonic mechanical vibrations, which are communicated distally through waveguide (54) to ultrasonic blade (56). Ultrasonic blade (56) is caused to oscillate longitudinally in the range of approximately 10 to 500 microns peak-to-peak, for example, and in some instances in the range of approximately 20 to 200 microns, at a predetermined vibratory frequency $f_o$ of approximately 50 kHz, for example. Vibrating ultrasonic blade (56) may be positioned in direct contact with tissue, with or without assistive clamping force provided by clamp arm (38), to impart ultrasonic vibrational energy to the tissue and thereby cut and/or seal the tissue.

Transducer housing (52) of removable acoustic assembly (14) includes a proximal stationary section (82) and a distal rotating section (84) rotatably coupled with proximal stationary section (82). Distal rotating section (84) is configured to rotate with ultrasonic transducer (50), waveguide (54), and inner shaft tube (62) relative to proximal stationary section (82). As shown in FIGS. 6 and 7, distal rotating section (84) houses transducer (50) and includes a cylindrical outer distal body (86), a cylindrical inner distal body (88) received within and threadedly coupled to outer distal body (86), and first and second annular gaskets (90, 92) arranged between outer and inner distal bodies (86, 88).

Proximal stationary section (82) of transducer housing (52) includes a cylindrical proximal body (94) and an adapter ring (96) received within proximal body (94) and coupled to a proximal face of inner distal body (88) with fasteners (98). As shown in FIG. 7, adapter ring (96) includes a proximal flange that couples proximal and distal housing sections (82, 84) together axially while permitting relative rotation therebetween. An annular rotation gasket (100) is positioned between a distal face of proximal body (94) and the proximal face of inner distal body (88) so as to encircle a cylindrical distal body portion of adapter ring (96). Rotation gasket (100) facilitates rotation of distal rotating section (84) relative to proximal stationary section (82). Proximal stationary section (82) further includes a proximal end cap (102) threadedly coupled with proximal body (94), and a plug (104) positioned within a central bore of end cap (102). Proximal stationary section (82) houses an electrical adapter (106) that couples to proximal electrical post (80) of ultrasonic transducer (50) and is configured to electrically couple with a power source (not shown).

Figure 8:
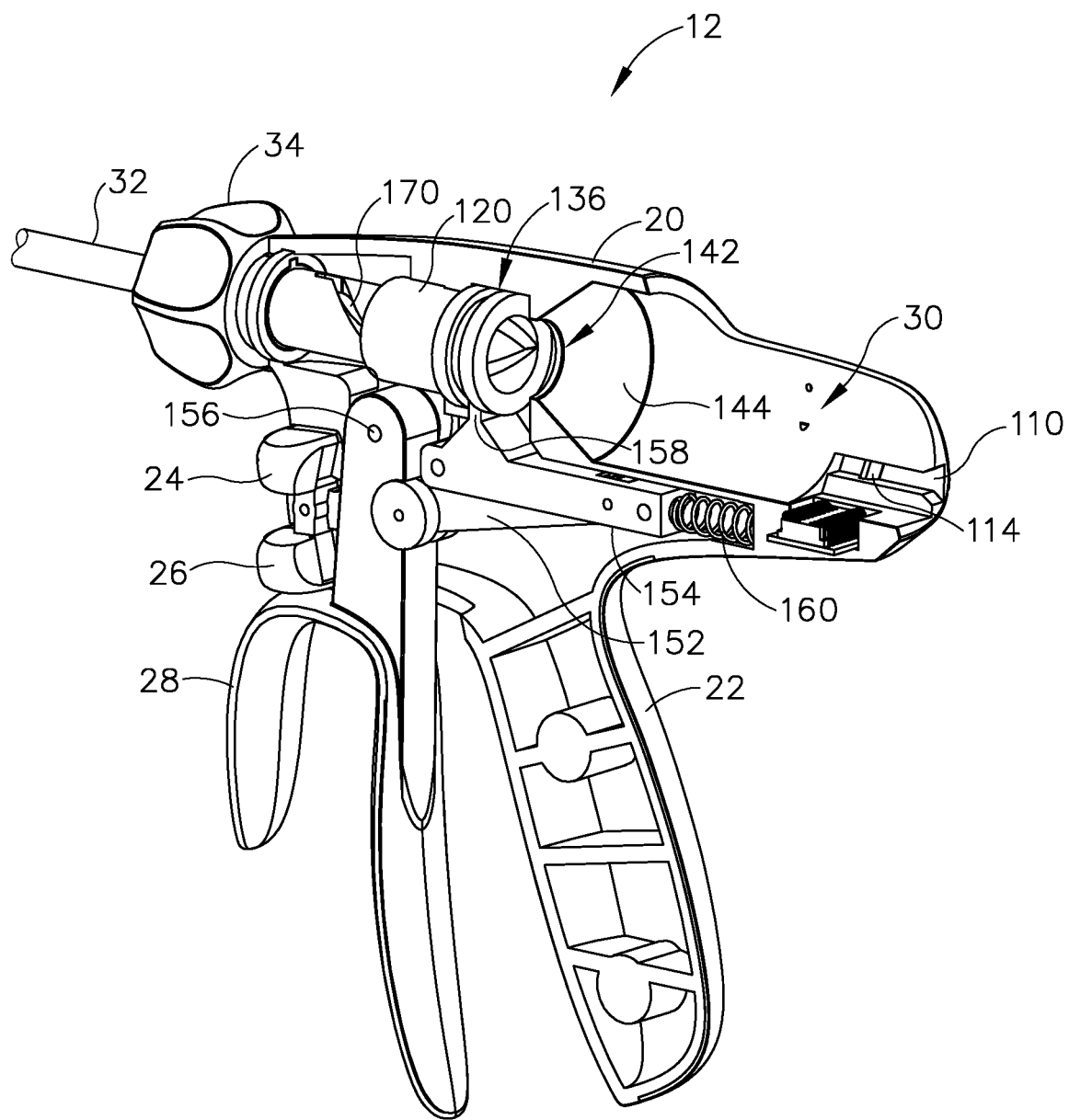
FIG. 8 depicts a side perspective view of the handle assembly of FIG. 2, with a side portion of the handle assembly being omitted.

An outer surface of proximal transducer housing section (82) includes a pair of axially extending coupling ribs (108) spaced circumferentially from one another on a lower side of proximal body (94). Each coupling rib (108) is configured to be slidably received within a respective coupling slot (110) formed in a sidewall of instrument body (20) and which is accessible via proximal body opening (30), as shown in FIG. 8. Each coupling slot (110) is closed at its outer lateral side by a respective coupling tab (112) having a projection (114) configured to releasably engage a notch (116) formed on a respective coupling rib (108) to thereby secure removable acoustic assembly (14) axially relative to handle assembly (12). Coupling tabs (112), shown best in FIGS. 1 and 2, are coupled to body (20) and are actuatable to selectively release and/or secure removable acoustic assembly (14) relative to handle assembly (12). Various other mechanisms suitable for releasably securing removably acoustic assembly (14) relative to handle assembly (12) will be readily apparent to those of ordinary skill in the art.

In various applications, removable acoustic assembly (14) may be provided to a user in a pre-assembled state such that no attachment and torqueing of waveguide (54) relative to ultrasonic transducer (50) must be performed by the user. This arrangement eliminates the risk of mechanical failure of acoustic assembly (14) during use otherwise caused by waveguide (54) being under-torqued or over-torqued to transducer (50) by the user.

C. Exemplary Handle Assembly Having Shaft Alignment Tube

During assembly of an acoustic assembly of an ultrasonic surgical instrument with its handle assembly, it is generally desirable to orient the ultrasonic blade in rotational alignment with the clamp arm. This ensures effective clamping of tissue captured between the clamp arm and the primary treatment surface of the blade, and resulting cutting and/or sealing of the clamped tissue. The features of ultrasonic surgical instrument (10) described below facilitate proper rotational alignment of clamp arm (38) with primary treatment surface (58) of ultrasonic blade (56), thereby ensuring optimal performance of surgical instrument (10).

FIG. 8 shows additional features of handle assembly (12) that facilitate rotational alignment of ultrasonic blade (56) with clamp arm (38) during assembly of removable acoustic assembly (14) with handle assembly (12). Body (20) of handle assembly (12) houses an alignment member in the form of a shaft alignment tube (120). As shown best in FIGS. 9 and 10, shaft alignment tube (120) includes a proximal tube portion (122), a medial tube portion (124), and a distal tube portion (126) formed integrally with one another. Proximal tube portion (122) is of the greatest diameter and has a pair of proximal and distal annular flanges (128, 129) spaced axially from one another so as to define an annular groove (130) therebetween. Medial tube portion (124) is of the smallest diameter, and distal tube portion (126) is of an intermediate diameter and includes a pair of axially extending ribs (132) arranged at diametrically opposed positions. A central passageway (134) extends axially through shaft alignment tube (120) and is configured to slidably receive waveguide (54) and inner shaft tube (62) therethrough, as described in greater detail below.

As shown in FIG. 8, shaft alignment tube (120) is supported within a distal portion of body (20) in coaxial alignment with outer shaft tube (32) and rotation knob (34). Annular flanges (128, 129) of proximal tube portion (122) are retained within a body pocket (136) having an axial length that is greater than an axial distance between outermost faces of annular flanges (128, 129), thereby permitting shaft alignment tube (120) to translate a predetermined axial distance relative to body (20) and rotation knob (34). Distal tube portion (126) is slidably received within a central bore of rotation knob (34), and axial ribs (132) are slidably received within respective axial grooves formed in an inner surface of rotation knob (34), as shown in FIG. 8. This configuration rotationally couples shaft alignment tube (120) with rotation knob (34) such that shaft alignment tube (120) and rotation knob (34) are configured to rotate together relative to body (20). Distal tube portion (126) is permitted to translate proximally and distally through rotation knob (34) by the predetermined axial distance described above.

Figure 10:
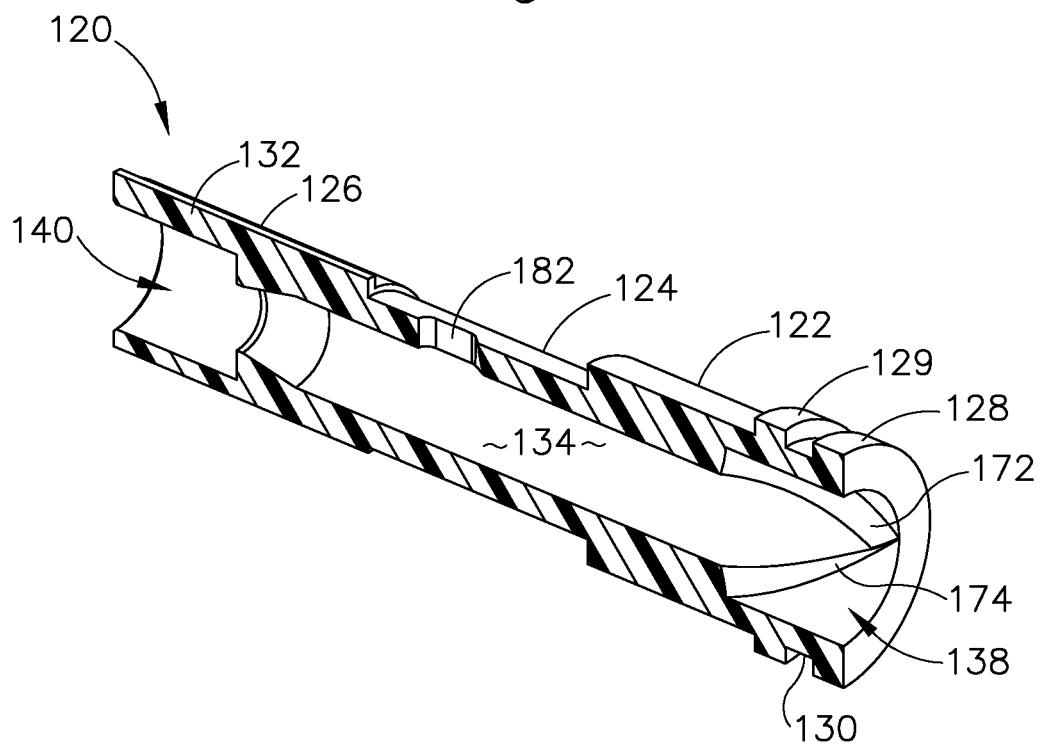
FIG. 10 depicts a cross-sectional side view of the alignment tube of FIG. 9.

As shown best in FIGS. 8 and 10, shaft alignment tube (120) includes a proximal tube opening (138) and a distal tube opening (140) that communicate via central passageway (134). Shaft alignment tube (120) is supported within body (20) such that proximal tube opening (138) opens to proximal body opening (30) through an interior wall opening (142) formed in a distally tapering conical wall (144) of body (20). Distal tube opening (140) is configured to receive a proximal end of outer shaft tube (32) so as to secure outer shaft tube (32) axially and rotationally to shaft alignment tube (120).

As shown in FIG. 8, handle assembly (12) houses a clamp actuation assembly (150) that comprises trigger (28), a link (152), a translating member (154), and shaft alignment tube (120). Trigger (28) is pivotably coupled to body (20) about a pivot joint (156), and is pivotably coupled to a distal end of link (152). A proximal end of link (152) is pivotably coupled to a proximal end of translating member (154). Translating member (154) is slidably disposed within body (20) and includes an upwardly extending protrusion (158) at a distal end thereof. Upwardly extending protrusion (158) is received within annular groove (130) of proximal tube portion (122) of shaft alignment tube (120), thereby coupling shaft alignment tube (120) and translating member (154) axially while still permitting shaft alignment tube (120) to rotate relative to translating member (154).

In use, pivoting trigger (28) toward pistol grip (22) drives link (152) and translating member (154) proximally, which in turn drives shaft alignment tube (120) proximally until proximal flange (128) abuts a proximal wall of body pocket (136). Proximal translation of shaft alignment tube (120) drives proximal translation of outer shaft tube (32) relative to connector tube (36) and inner shaft tube (62), thereby pivoting clamp arm (38) toward ultrasonic blade (56). Pivoting trigger (28) away from pistol grip (22) drives link (152), translating member (154), alignment tube (120), and outer shaft tube (32) distally, which causes clamp arm (38) to pivot away from ultrasonic blade (56). In the present example, a compression spring (160) is arranged between the proximal end of translating member (154) and an inner surface of body (20) so as to bias translating member (154) distally, and thus clamp arm (38) toward its open position. In other examples, actuation assembly (150) may further include a force-limiting feature configured to limit the maximum clamping force applicable to tissue with clamp arm (38), such as a spring stack similar to spring stack (266) described below, for example.

Figure 9:
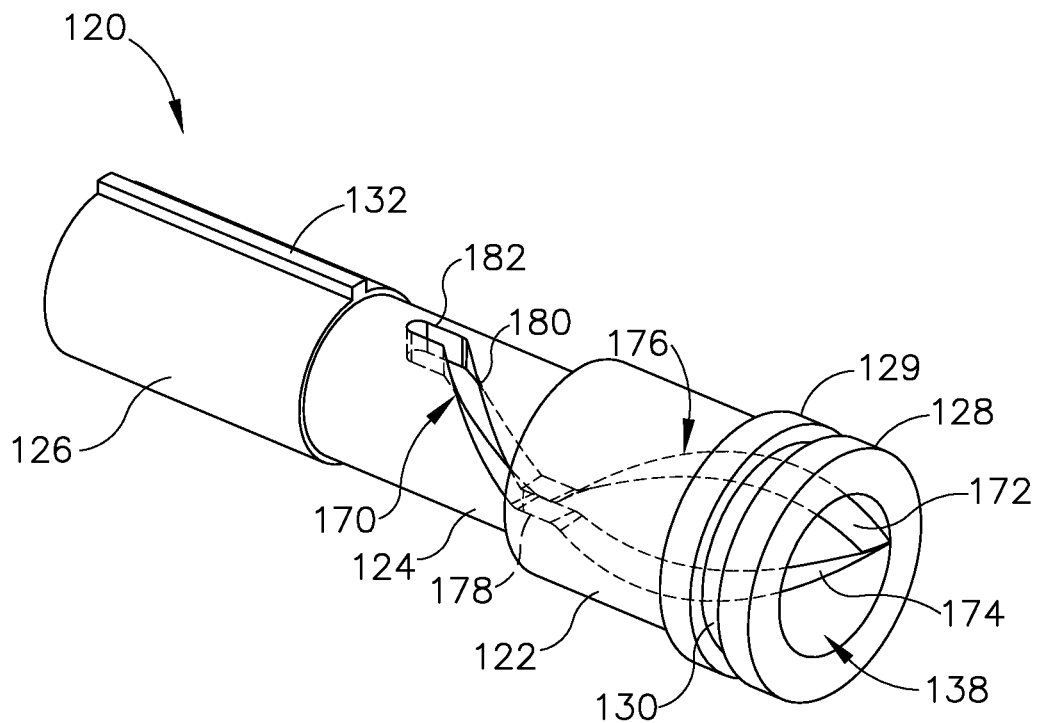
FIG. 9 depicts a perspective view of an alignment tube of the handle assembly of FIG. 2.

As best shown in FIGS. 9 and 10, shaft alignment tube (120) further includes an alignment slot (170). Alignment slot (170) is configured to receive and guide alignment pin (66) of removable acoustic assembly (14) when removable acoustic assembly (14) is coupled with handle assembly (12) in a proximal to distal direction. In this manner, alignment slot (170) dictates a rotational orientation of waveguide (54) and inner shaft tube (62) relative to shaft alignment tube (120) and outer shaft tube (32) as alignment pin (66) travels distally through alignment slot (170), as described in greater detail below. It will be appreciated that in other versions, alignment slot (170) may be incorporated into removable acoustic assembly (14) while a protrusion functionally similar to alignment pin (66) may be incorporated within the interior of handle assembly (12).

Alignment slot (170) is defined by first and second camming surfaces (172, 174) that extend distally through proximal and medial tube portions (122, 124), along a sidewall of shaft alignment tube (120). Alignment slot (170) includes a proximal angular slot portion (176) that opens to proximal tube opening (138), a proximal axial slot portion (178) extending distally from proximal angular slot portion (176), a distal angular slot portion (180) extending distally from proximal axial slot portion (178), and a distal axial slot portion (182) extending distally from distal angular slot portion (180). As used herein in connection with angular slot portions (176, 180), the term "angular" means non-parallel to a central axis of shaft alignment tube (120). For example, as shown in FIG. 9, angular slot portions (176, 178) each extend circumferentially about the central axis of shaft alignment tube (120), while also traveling distally. In contrast, axial slot portions (178, 182) each extend axially, parallel to a central axis of shaft alignment tube (120). Accordingly, as described in greater detail below, angular slot portions (176, 178) are each configured to direct simultaneous rotation and translation of waveguide (54) and inner shaft tube (62) relative to outer shaft tube (32) and shaft alignment tube (120). By comparison, axial slot portions (178, 182) are each configured to direct only translation of waveguide (54) and inner shaft tube (62) relative to outer shaft tube (32) and shaft alignment tube (120).

As shown in FIG. 9, proximal ends of first and second camming surfaces (172, 174) are adjacent to one another on an interior of a first lateral side of shaft alignment tube (120) at proximal tube opening (138). As camming surfaces (172, 174) extend distally to define proximal angular slot portion (176), first camming surface (172) travels circumferentially along the tube interior in a counter-clockwise direction, while second camming surface (174) travels circumferentially along the tube interior in a clock-wise direction. Camming surfaces (172, 174) reach an opposed second lateral side of shaft alignment tube (120) and then extend axially together to define proximal axial slot portion (178). From proximal axial slot portion (178), camming surfaces extend distally and clockwise together toward distal axial slot portion (182) arranged on an upper side of medial tube portion (124). In the present example, proximal axial slot portion (178) is angularly offset from the proximal ends of camming surfaces (172, 174) by approximately 180 degrees. Additionally, distal axial slot portion (182) is angularly offset from proximal axial slot portion (178) by approximately 90 degrees.

D. Mating of Removable Acoustic Assembly with Handle Assembly

FIGS. 11-15B show an exemplary process for mating removable acoustic assembly (14) with handle assembly (12), and rotationally coupling outer shaft tube (32) with inner shaft tube (62). As described below, the alignment features of removable acoustic assembly (14) and handle assembly (12) ensure that and clamp arm (38) and primary blade treatment surface (58) of ultrasonic blade (56) are oriented in rotational alignment with one another when removable acoustic assembly (14) is fully coupled with handle assembly (12).

Figure 11:
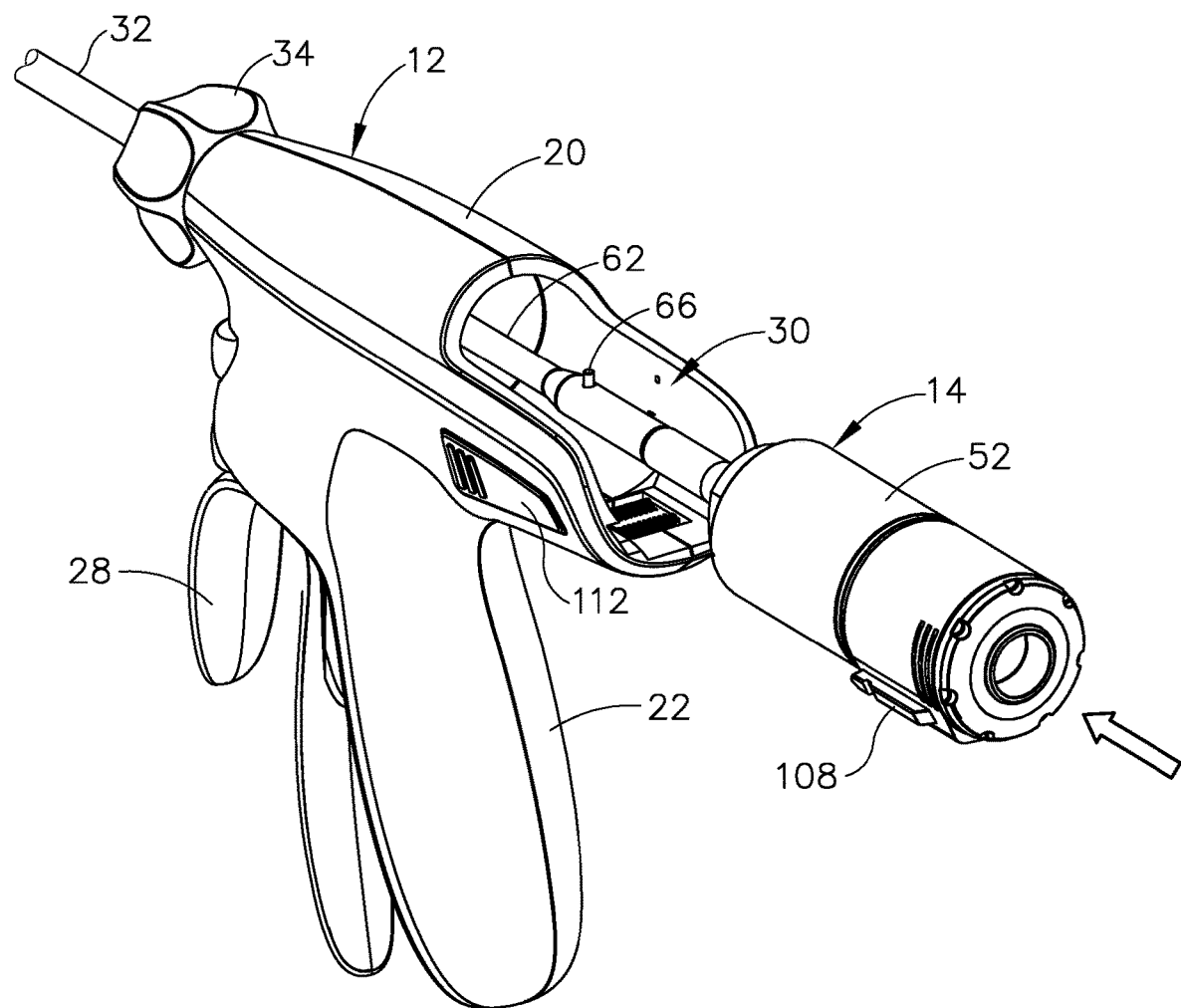
FIG. 11 depicts a rear perspective view of the ultrasonic surgical instrument of FIG. 2, showing the removable assembly being assembled with the handle assembly.
Figure 12A:
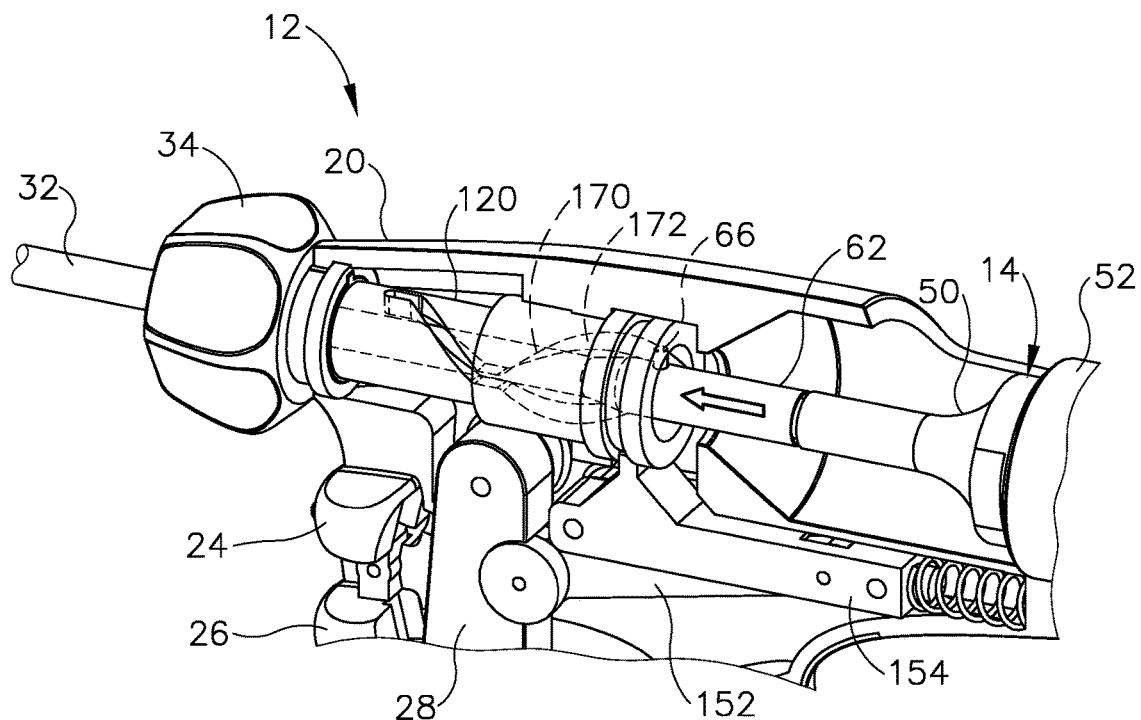
FIG. 12A depicts a side elevational view of the handle assembly and removable assembly of FIG. 2, with a side portion of the handle assembly being omitted, showing an alignment pin of the removable assembly in a proximal pin position within an alignment slot of the alignment tube of the handle assembly.

As shown in FIGS. 2, 11, and 12A, a distal end of removable acoustic assembly (14), defined by ultrasonic blade (56) and the distal end of inner shaft tube (62), is directed distally through proximal body opening (30) of handle assembly (12) and into central passageway (134) of shaft alignment tube (120), via interior wall opening (142) and proximal tube opening (138). Tapered conical wall (144) of body (20) is configured to direct ultrasonic blade (56) into central passageway (134). As removable acoustic assembly (14) is advanced distally relative to handle assembly (12), ultrasonic blade (56) and the distal end of inner shaft tube (62) pass fully through shaft alignment tube (120) and into outer shaft tube (32), such that outer shaft tube (32) and the components of removable acoustic assembly (14) are arranged coaxially.

Figure 12B:
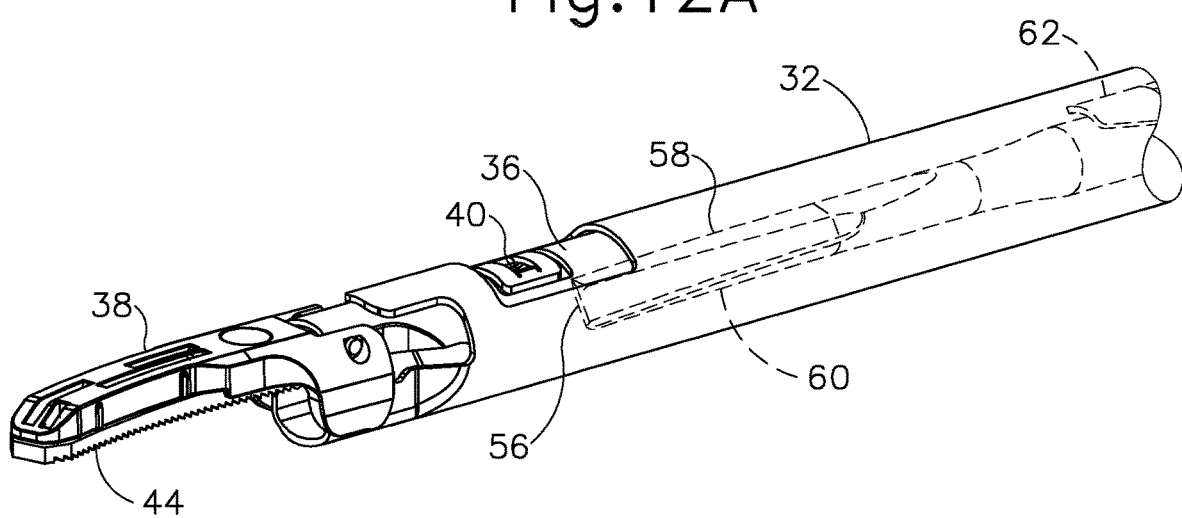
FIG. 12B depicts a perspective view of a distal end of the ultrasonic surgical instrument of FIG. 1, showing an ultrasonic blade of the removable assembly in a first orientation corresponding to the proximal pin position of FIG. 12A.

As shown in FIG. 12A, continued distal advanced of removable acoustic assembly (14) directs alignment pin (66) through proximal tube opening (138) of shaft alignment tube (120). If waveguide (54) and inner shaft tube (62) are oriented rotationally such that there is any degree of rotational offset between alignment pin (66) and proximal axial slot portion (178) of alignment slot (170), alignment pin (66) will contact one of camming surfaces (172, 174). In the illustrated example, waveguide (54) and inner shaft tube (62) are oriented as shown in FIG. 12B such that alignment pin (66) extends upwardly and confronts first camming surface (172), as shown in FIG. 12A.

Figure 13A:
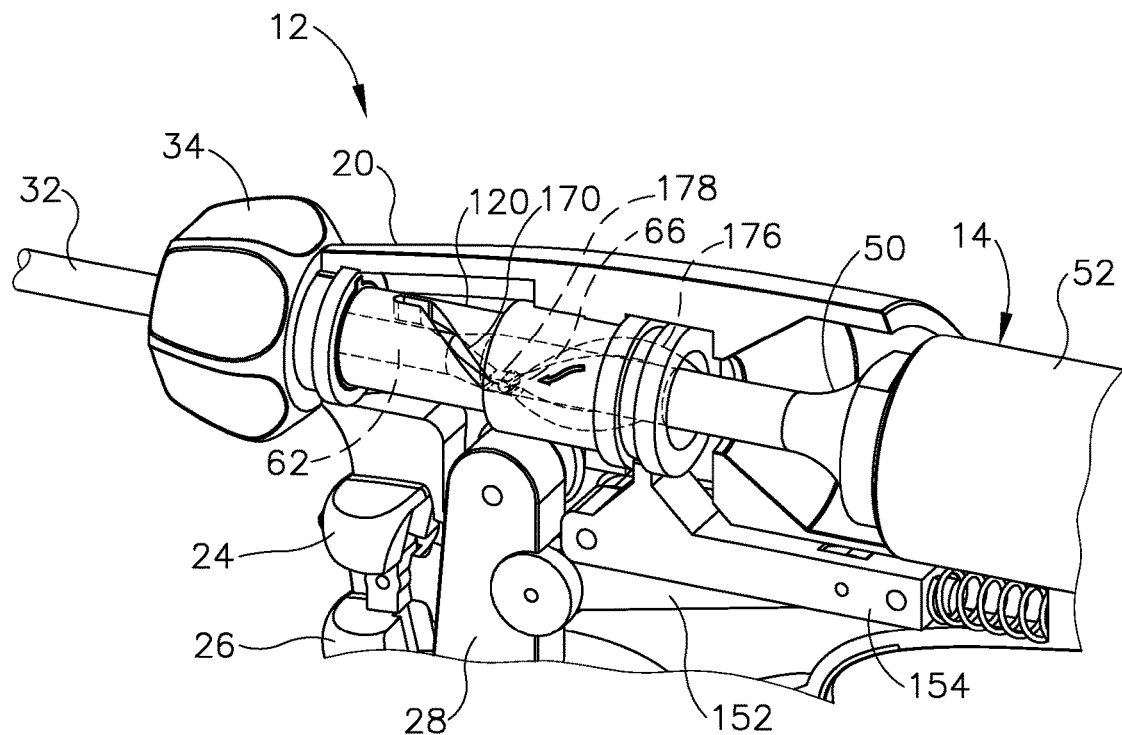
FIG. 13A depicts a side elevational view of the handle assembly and removable assembly of FIG. 2, showing the alignment pin in a medial pin position within the alignment slot of the alignment tube.
Figure 13B:
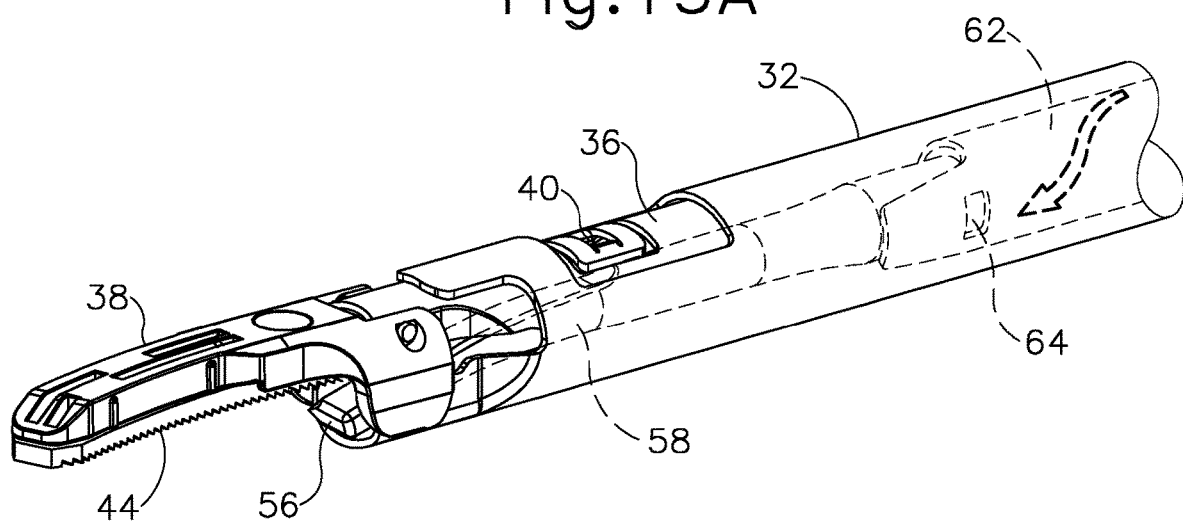
FIG. 13B depicts a perspective view of the distal end of the ultrasonic surgical instrument of FIG. 2, showing the ultrasonic blade in a second orientation corresponding to the medial pin position of FIG. 13A.

As shown in FIG. 13A, acoustic assembly (14) is pushed further distally into handle assembly (12) so that first camming surface (172) contacts and directs alignment pin (66) in a counter-clockwise direction toward proximal axial slot portion (178). As shown in FIG. 13B, this camming action causes waveguide (54) and inner shaft tube (62) to rotate counter-clockwise by approximately 90 degrees so that primary blade treatment surface (58) of ultrasonic blade (56) is oriented generally perpendicularly to clamp arm (38), as shown in FIG. 13B. As alignment pin (66) continues distally through proximal axial slot portion (178), ultrasonic blade (56) passes freely through the distal ends of outer shaft tube (32) and connector tube (36), without interference otherwise caused by the lateral curvature of blade (56).

As described above, in the present example waveguide (54) and inner shaft tube (62) are inserted into shaft alignment tube (120) in a starting rotational orientation in which the exposed portion of alignment pin (66) extends generally upwardly such that pin (66) contacts and travels distally along first camming surface (172), in a counter-clockwise direction. In other examples, waveguide (54) and inner shaft tube (62) may be provided in a starting rotational orientation in which the exposed portion of alignment pin (66) extends generally downwardly such that pin (66) contacts and travels distally along second camming surface (174), in a clockwise direction. Accordingly, and advantageously, first and second camming surfaces (172, 174) are configured to contact and direct alignment pin (66) distally and circumferentially into alignment with proximal axial slot portion (178), such that primary blade treatment surface (58) is oriented perpendicularly to clamp arm (38), given any degree of rotational offset between alignment pin (66) and proximal axial slot portion (178).

Figure 14A:
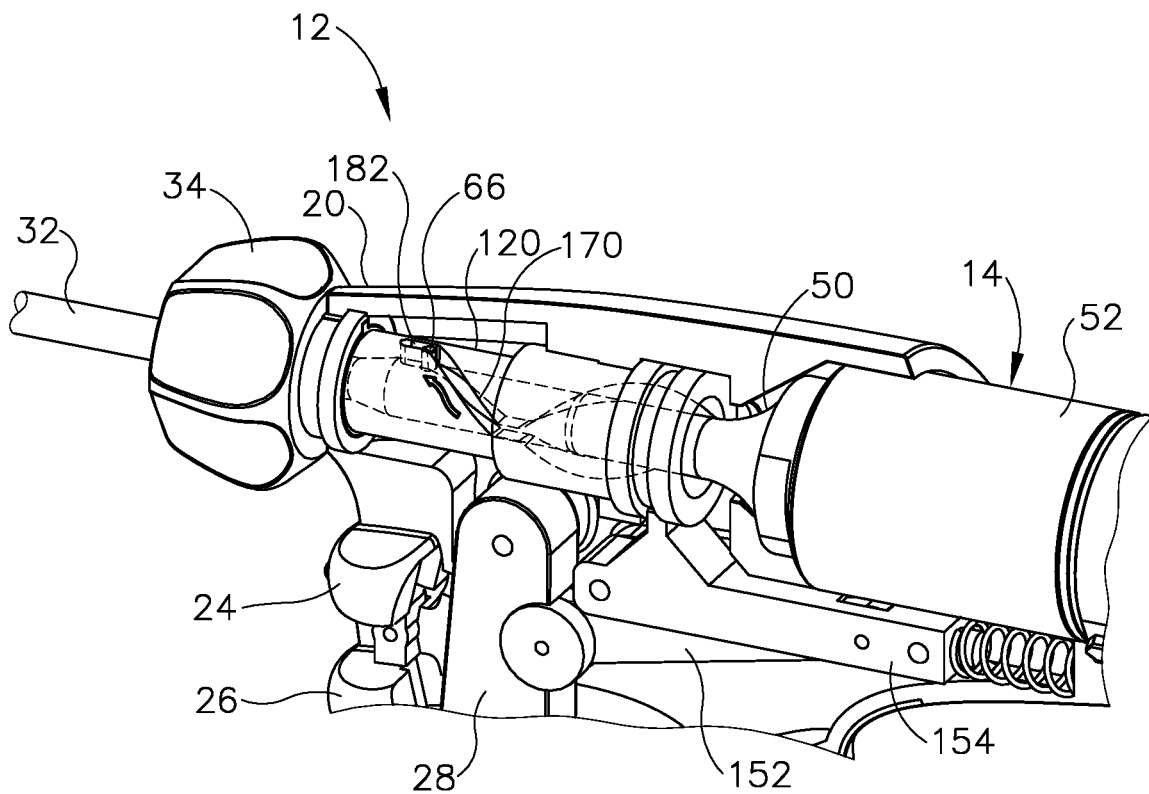
FIG. 14A depicts a side elevational view of the handle assembly and removable assembly of FIG. 2, showing the alignment pin in a first distal pin position within the alignment slot of the alignment tube.
Figure 14B:
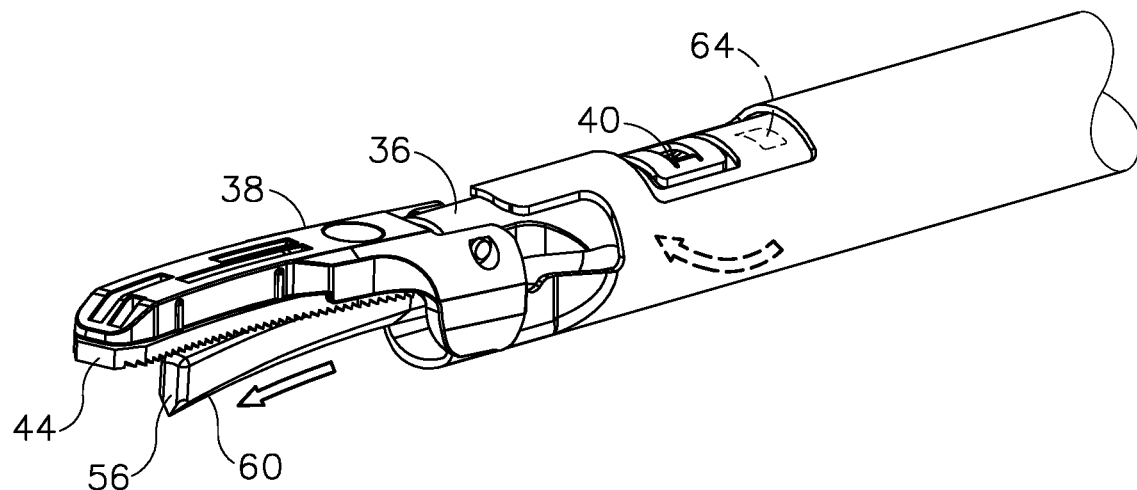
FIG. 14B depicts a perspective view of the distal end of the ultrasonic surgical instrument of FIG. 2, showing the ultrasonic blade in a third orientation corresponding to the first distal pin position of FIG. 14A.

As shown in FIG. 14A, acoustic assembly (14) is pushed further distally into handle assembly (12) so that alignment pin (66) passes distally through distal angular slot portion (180) and toward distal axial slot portion (182). As shown in FIG. 14B, this step causes waveguide (54) and inner shaft tube (62) to advance distally and simultaneously rotate clockwise by approximately 90 degrees so that primary blade treatment surface (58) is oriented in rotational alignment with and thereby confronts clamp arm (38). As shown in FIG. 14A, removable acoustic assembly (14) is now fully seated within handle assembly (12) such that coupling ribs (108) of proximal transducer housing section (82) are fully received within coupling slots (110). In this state, rib notches (116) lockingly engage tab projections (114) of coupling tabs (112), thereby securing removable acoustic assembly (14) axially relative to handle assembly (12). As shown in FIG. 14B, however, the distal tip of ultrasonic blade (56) remains proximally spaced from the distal tip of clamp arm (38).

Figure 15A:
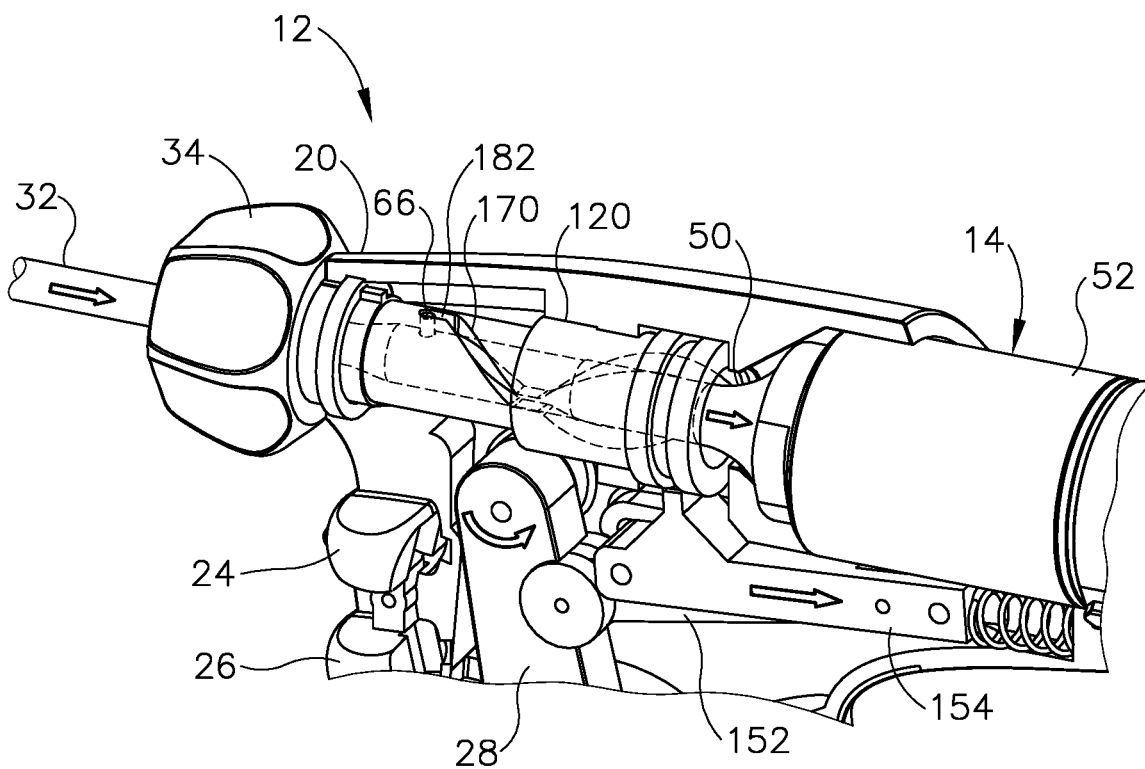
FIG. 15A depicts a side elevational view of the handle assembly and removable assembly of FIG. 2, showing the alignment pin in a second distal pin position within the alignment slot of the alignment tube.
Figure 15B:
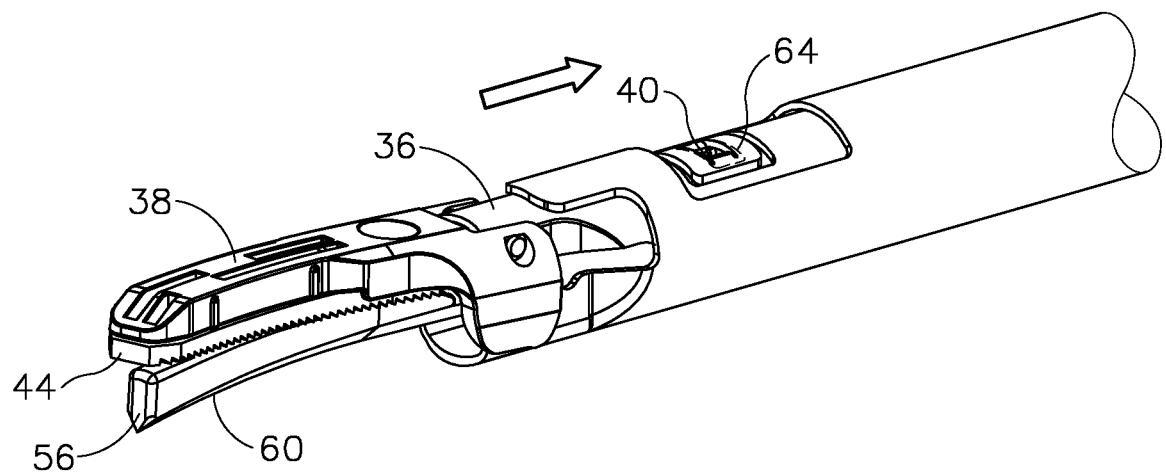
FIG. 15B depicts a perspective view of the distal end of the ultrasonic surgical instrument of FIG. 2, showing the ultrasonic blade in a fourth orientation corresponding to the second distal pin position of FIG. 15A.

As shown in FIG. 15A, in order to axially align the distal tips of ultrasonic blade (56) and clamp arm (38), trigger (28) is squeezed toward pistol grip (22) to draw shaft alignment tube (120) proximally until alignment pin (66) abuts a distal end of distal axial slot portion (182). This motion draws outer shaft tube (32) and connector tube (36) proximally relative to inner shaft tube (62) so that snap arm (40) of connector tube (36) snaps into distal opening (64) of inner shaft tube (62), as shown in FIG. 15B. This snap-fit engagement couples connector tube (36) axially and rotationally relative to inner shaft tube (62). As a result, this engagement also rotationally couples the distal end of inner shaft tube (62) with the distal end of outer shaft tube (32), via connector tube (36) and clevis arms (46) of clamp arm (38). Connector tube (36) is further restrained proximally relative to the distal end of inner shaft tube (62) via connector tube tab (41), shown in FIG. 4.

It will be appreciated that inner and outer shaft tubes (32, 62) are rotationally coupled together at their proximal ends by engagement of alignment pin (66) with the lateral sides of distal axial slot portion (182) of shaft alignment tube (120), which is rotationally coupled with outer shaft tube (32) as described above. Accordingly, any rotational input applied to rotation knob (34) is transferred to all rotatable components of instrument (10), including outer shaft tube (32), inner shaft tube (62), waveguide (54), shaft alignment tube (120), ultrasonic transducer (50), and distal transducer housing section (84).

The mechanical grounding of connector tube (36) to inner shaft tube (62) as described above enables outer shaft tube (32) to be actuated axially relative to connector tube (36) to thereby pivot clamp arm (38) between open and closed positions relative to ultrasonic blade (56) while clamp arm (38) remains in rotational alignment with primary blade treatment surface (58). In particular, as outer shaft tube (42) is actuated proximally by squeezing trigger (28) toward pistol grip (22), connector tube (36) remains axially fixed by its connection to inner shaft tube (62), which is axially fixed relative to body (20), via snap arm (40) and tab (41). Accordingly, clamp arm (38) pivots about pivot pin (48) from an open position to a closed position against primary blade treatment surface (58). When trigger (28) is released and moves away from pistol grip (22), outer shaft tube (32) actuates distally relative to connector tube (36), thereby pivoting clamp arm (38) to an open position.

Following completion of a surgical procedure, removable acoustic assembly (14) may be separated from handle assembly (12) by depressing coupling tabs (112) to thereby disengage tab projections (114) from coupling ribs (108) of proximal transducer housing section (82). Simultaneously, connector tube snap arm (40) is disengaged from distal opening (64) of inner shaft tube (62), and removable acoustic assembly (14) is drawn proximally. As acoustic assembly (14) is withdrawn proximally from handle assembly (12), alignment pin (66) travels proximally through alignment slot (170), thereby rotating ultrasonic blade (56) in directions opposite those described above, to enable blade (56) to pass freely back through outer shaft tube (32).

II. Exemplary Ultrasonic Surgical Instrument Having Removable Clamp Assembly

A. Overview of Ultrasonic Surgical Instrument

Figure 16:
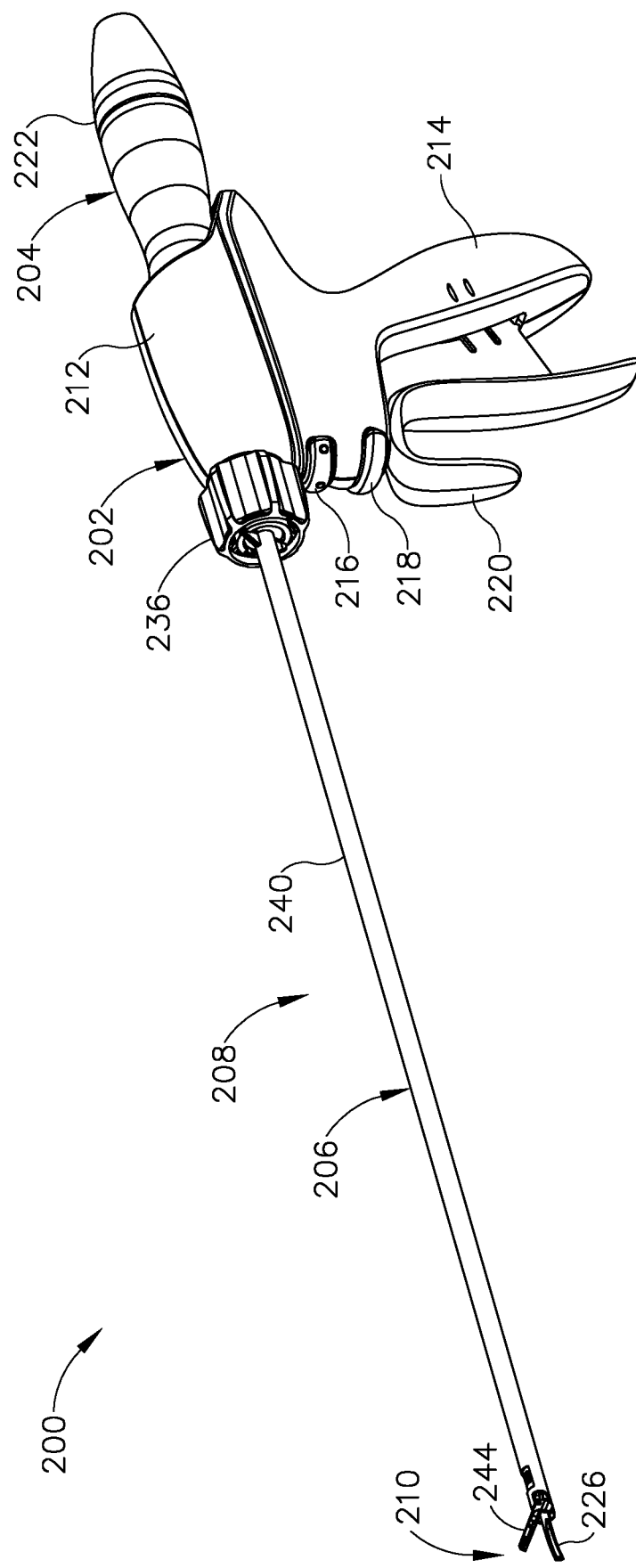
FIG. 16 depicts a perspective view of another exemplary ultrasonic surgical instrument.
Figure 17:
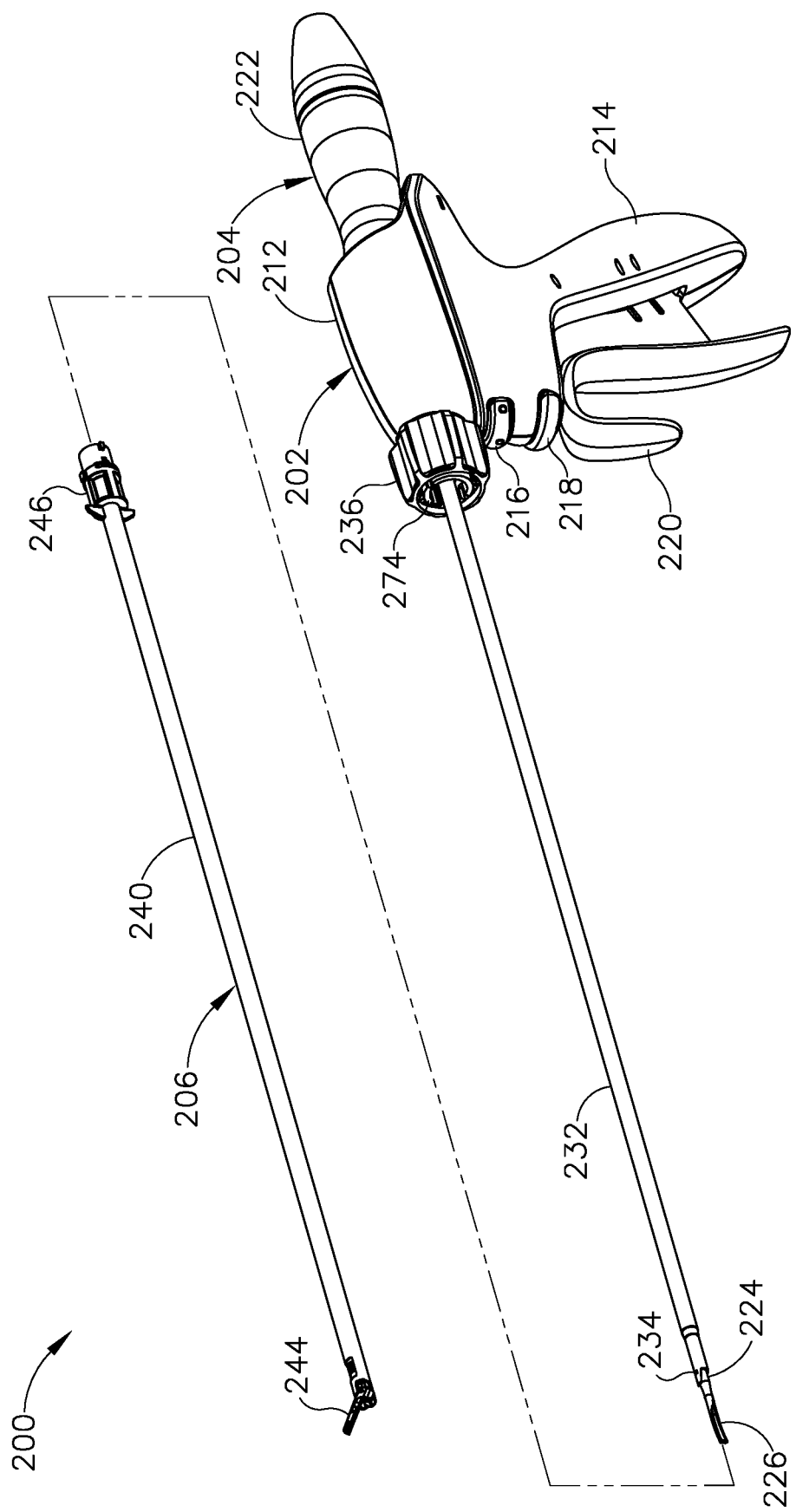
FIG. 17 depicts a perspective disassembled view of the ultrasonic surgical instrument of FIG. 16, having a handle assembly and a removable assembly.

FIGS. 16 and 17 show another exemplary ultrasonic surgical instrument (200) that is similar to instrument (10) described above in that instrument (200) has an arrangement of alignment features that ensure proper rotational and axial alignment of a clamp arm (244) with an ultrasonic blade (226) of instrument (200). Additionally, as described in greater detail below, the alignment features of instrument (200) prohibit actuation of clamp arm (244) relative to ultrasonic blade (226) until full rotational and axial alignment has been achieved, thereby ensuring effective clamping and resulting treatment of tissue captured between clamp arm (244) and ultrasonic blade (226).

Ultrasonic surgical instrument (200) includes a handle assembly (202), an acoustic assembly (204) coupled to the handle assembly (202), and a removable clamp assembly (206) configured to selectively couple with and decouple from handle assembly (202). In the assembled state shown in FIG. 16, surgical instrument (200) presents a shaft assembly (208) extending distally from handle assembly (202), and an end effector (210) arranged at a distal end of shaft assembly (208). Handle assembly (202) is similar to handle assembly (12) in that handle assembly (202) comprises a body (212) including a pistol grip (214) and energy control buttons (126, 218) configured to be manipulated by a surgeon to control various aspects of ultrasonic energy delivered by surgical instrument (200). A trigger (220) is pivotably coupled to a lower portion of body (212) and is pivotable toward and away from pistol grip (214) to selectively actuate end effector (210).

Figure 23A:
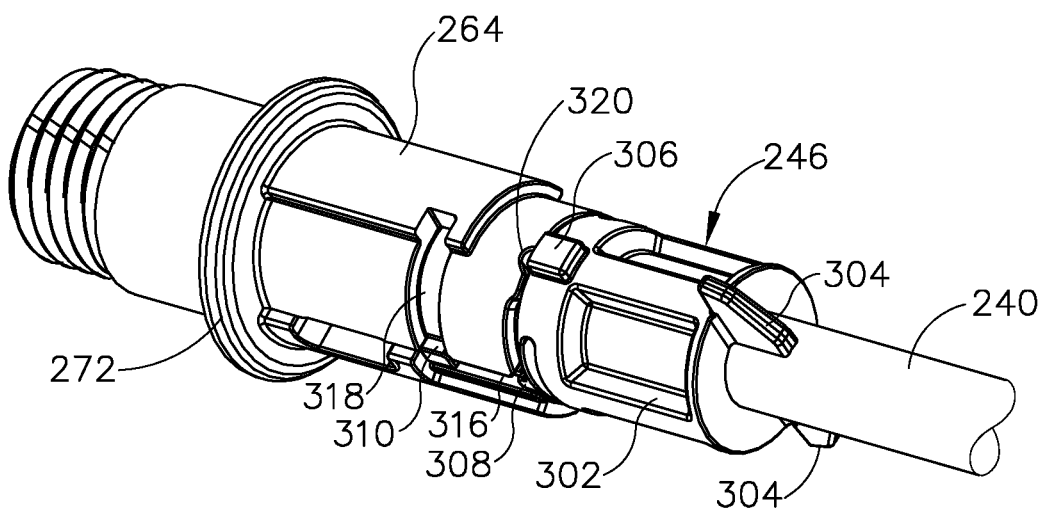
FIG. 23A depicts a perspective view of the alignment plug and the inner alignment tube of FIG. 22B, with the outer guide tube being omitted, showing the alignment plug in the first rotational position.
Figure 23B:
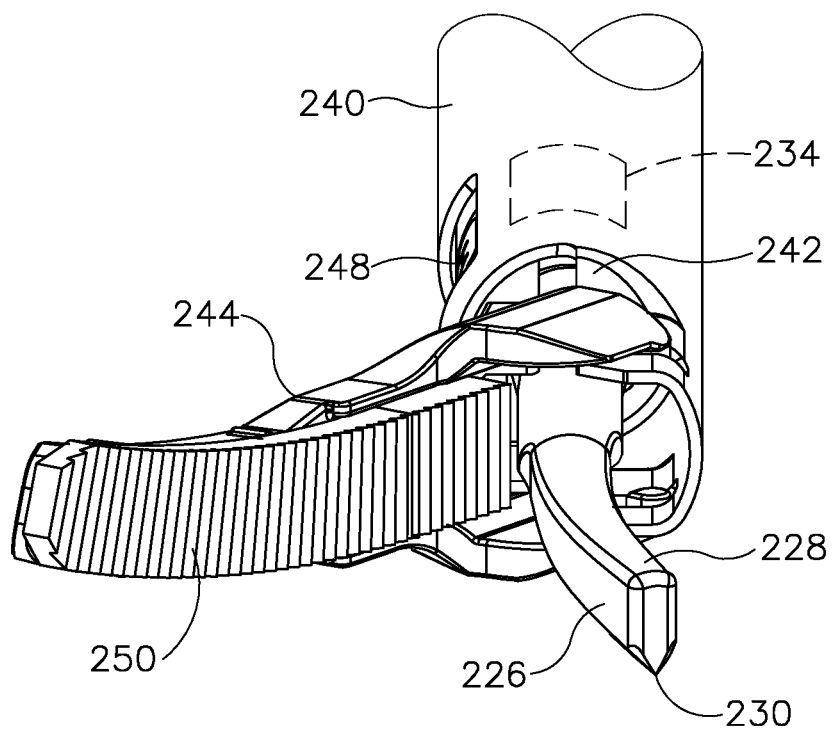
FIG. 23B depicts a perspective view of an end effector of the ultrasonic surgical instrument of FIG. 16, showing the clamp arm in a first orientation corresponding to the first alignment plug position of FIG. 23A.

Acoustic assembly (204) is shown coupled with handle assembly (202) includes a detachable ultrasonic transducer (222) (or "handpiece"), an ultrasonic waveguide (224) acoustically coupled to and extending distally from a distal end of transducer (222), and an ultrasonic blade (226) formed integrally with and extending distally from a distal end of waveguide (224). Transducer (222) may include components similar to those of transducer (50) described above, and transducer (222) is configured to drive (i.e., vibrate) waveguide (224) and blade (226) at ultrasonic frequencies for cutting and/or sealing tissue positioned in contact with blade (226). Similar to ultrasonic blade (56), ultrasonic blade (226) extends distally with a lateral curvature and includes a primary blade treatment surface (228) arranged on an upper side of blade (226), and a lower cutting edge (230) arranged on an opposing lower side of blade (226), as also seen in FIGS. 23B and 24B. Transducer (222) is releasably coupled to a proximal end of waveguide (224), for example by threaded engagement, and is releasably supported by body (212) such that transducer (222) may be separated from waveguide (224) and body (212), if desired.

As shown in FIG. 17, an inner shaft tube (232) of shaft assembly (208) extends distally from handle assembly (202) and houses waveguide (224). Waveguide (224) may be supported within inner shaft tube (232) by a plurality of nodal support elements (not shown) positioned at various locations along a length of waveguide (224) corresponding to acoustic nodes. An upper side of a distal end of inner shaft tube (232) includes an opening (234) configured to facilitate coupling of inner shaft tube (232) with an outer shaft tube (240) of removable clamp assembly (206), described below. Inner shaft tube (232) and waveguide (224) are secured axially and are rotatable relative to handle assembly (202) by a rotation knob (236).

Figure 18:
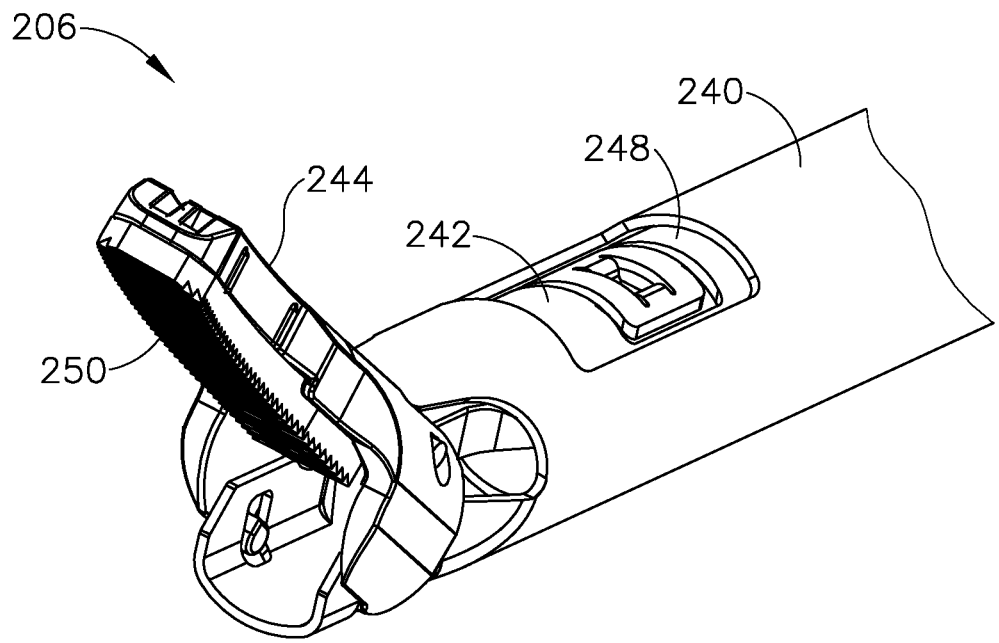
FIG. 18 depicts a perspective view of an outer shaft tube, a connector tube, and a clamp arm of the ultrasonic surgical instrument of FIG. 16.
Figure 19:
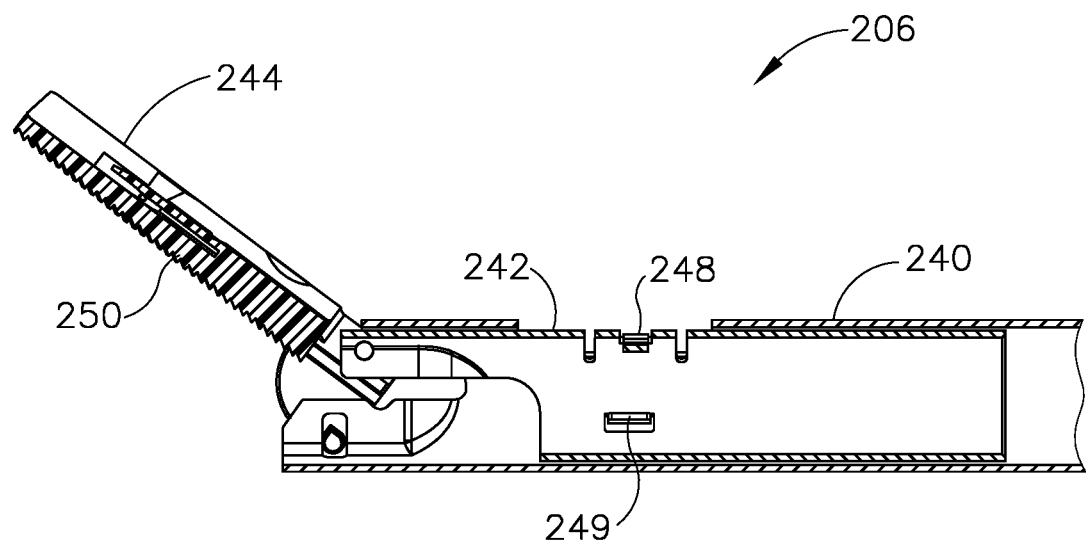
FIG. 19 depicts a side cross-sectional view of the outer shaft tube, connector tube, and clamp arm of FIG. 18.

As shown in FIGS. 17-19, removable clamp assembly (206) comprises an outer shaft tube (240) of shaft assembly (208), a distal connector tube (242) and a clamp arm (244) coupled to a distal end of outer shaft tube (240), and an alignment plug (246) coupled to a proximal end of outer shaft tube (240). Connector tube (242) includes a snap arm (248) and inwardly extending tab (249), and is generally similar in structure and function to connector tube (36) described above. Clamp arm (244) includes a clamp pad (250) and is generally similar in structure and function to clamp arm (38) described above. When instrument (200) is in an assembled, operational state as shown in FIG. 16, outer shaft tube (240) is configured to translate proximally and distally relative to inner shaft tube (232) and connector tube (242) to thereby actuate clamp arm (244) relative to ultrasonic blade (226), in a manner similar to that described above in connection with instrument (10).

B. Clamp Actuation Assembly of Ultrasonic Surgical Instrument

Figure 20:
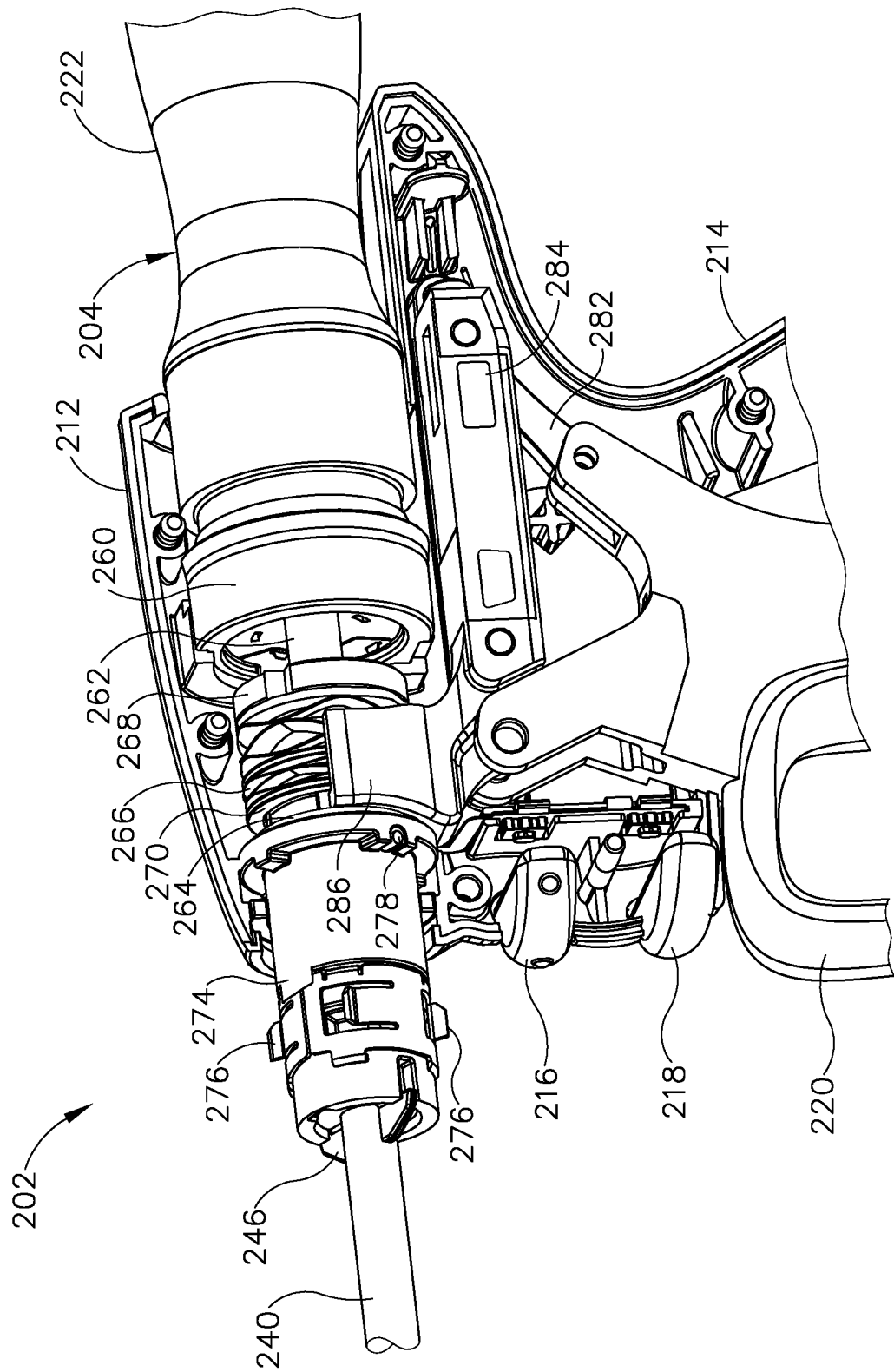
FIG. 20 depicts a perspective view of the ultrasonic surgical instrument of FIG. 16, with a side portion of the handle assembly and a rotation knob being omitted.
Figure 21:
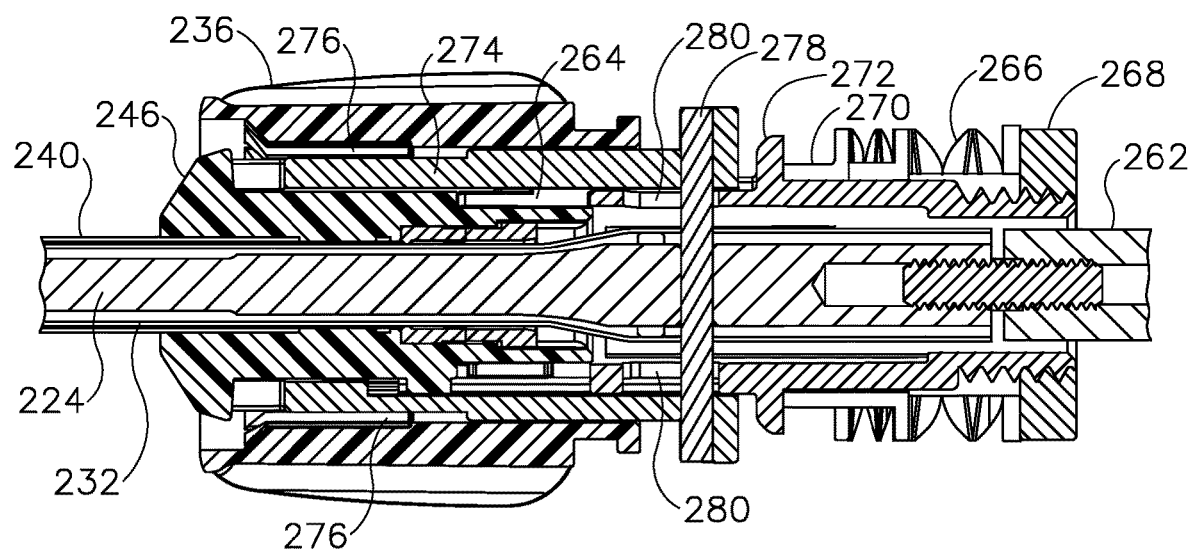
FIG. 21 depicts a side cross-sectional view of select portions of removable assembly and handle assembly in a mated configuration.

FIGS. 20 and 21 show additional details of ultrasonic surgical instrument (200) in an assembled and operational state, including features of handle assembly (202) that facilitate actuation of clamp arm (244). As shown in FIG. 20, a distal end of ultrasonic transducer (222) is supported by a support collar (260) coupled to body (212). A distal end (or "horn") (262) of transducer (222) extends distally through annular support collar (260) and into a proximal end of a shaft alignment tube (264), where transducer horn (262) threadedly couples with a proximal end of waveguide (224). A proximal portion of shaft alignment tube (264) is encircled by a spring stack (266) comprising a linear array of adjacent waves springs. Spring stack (266) is retained at a proximal end by an adjustable retaining nut (268) threaded coupled to shaft alignment tube (264), and at a distal end by a translating ring (270) that abuts a medial flange (272) of shaft alignment tube (264).

A distal portion of shaft alignment tube (264) extending distally from medial flange (272) is received within an outer guide tube (274). Outer guide tube (274) is coupled axially and rotationally to rotation knob (236) by a pair of clips (276) that extend circumferentially about outer guide tube (274). Outer guide tube (274) is coupled rotationally to shaft alignment tube (264), inner shaft tube (232), and waveguide (224) by a coupling pin (278) that extends transversely through these components. A proximal portion of shaft alignment tube (264) includes a pair of axially extending pin slots (280) through which coupling pin (278) extends. Pin slots (280) permit shaft alignment tube (264) to translate proximally and distally relative to outer guide tube (274), inner shaft tube (232), and waveguide (224). As described in greater detail below, the proximal portion of shaft alignment tube (264) further includes features configured to interlock with alignment plug (246) so that shaft alignment tube (264), alignment plug (246), and outer shaft tube (240) may translate proximally and distally relative to handle assembly body (212) to actuate clamp arm (244).

As shown in FIG. 20, trigger (220) is pivotably coupled to a link (282), which in turn is pivotably coupled to a translating member (284) having a distal yoke (286) that engages a distal face of translating ring (270) to define a clamp actuation assembly. When trigger (220) is squeezed toward pistol grip (214), yoke (286) drives translating ring (270) proximally against spring stack (266). Spring stack (266) is configured to resist compression up to a predetermined force threshold, and thereby transfer the proximal motion to shaft alignment tube (264) via retaining nut (268), which in turn transfers the proximal motion to alignment plug (246) and outer shaft tube (240). As described above, proximal translation of outer shaft tube (240) relative to inner shaft tube (232) causes clamp arm (244) to pivot toward ultrasonic blade (226) to clamp tissue therebetween.

Spring stack (266) is configured to limit the maximum clamping force exerted by clamp arm (244). In particular, when the proximally-directed force exerted on spring stack (266) by yoke (286) exceeds the predetermined force threshold described above, for example when clamp arm (244) encounters substantial resistance to further pivoting toward ultrasonic blade (226), spring stack (266) will compress to thereby limit the transfer of the proximally-directed force to outer shaft tube (240) and clamp arm (244). More specifically, when the force threshold is reached, spring stack (266) will compress proximally against retaining nut (268) while retaining nut (268) and shaft alignment tube (264) remain stationary relative to handle assembly body (212). Accordingly, when the force threshold is reached, trigger (220) will continue to advance toward pistol grip (214), but clamp arm (244) will cease further pivotal movement toward ultrasonic blade (226). Retaining nut (268) may be selectively rotated into more or less threaded engagement with shaft alignment tube (264) to thereby adjust the force threshold. For example, nut (268) may be rotated to further threadedly engage shaft alignment tube (264) and compress spring stack (266) against translating ring (270) and yoke (286) with a desired amount of pre-load to thereby increase the force threshold.

C. Shaft Alignment Features of Ultrasonic Surgical Instrument

FIGS. 22A-24B show additional features of shaft alignment tube (264) and outer guide tube (274) of handle assembly (202), and alignment plug (246) of removable clamp assembly (206). As described below, features of these components facilitate proper alignment of clamp arm (244) with primary blade treatment surface (228) of ultrasonic blade (226) when removable clamp assembly (206) is coupled with handle assembly (202).

Figure 22A:
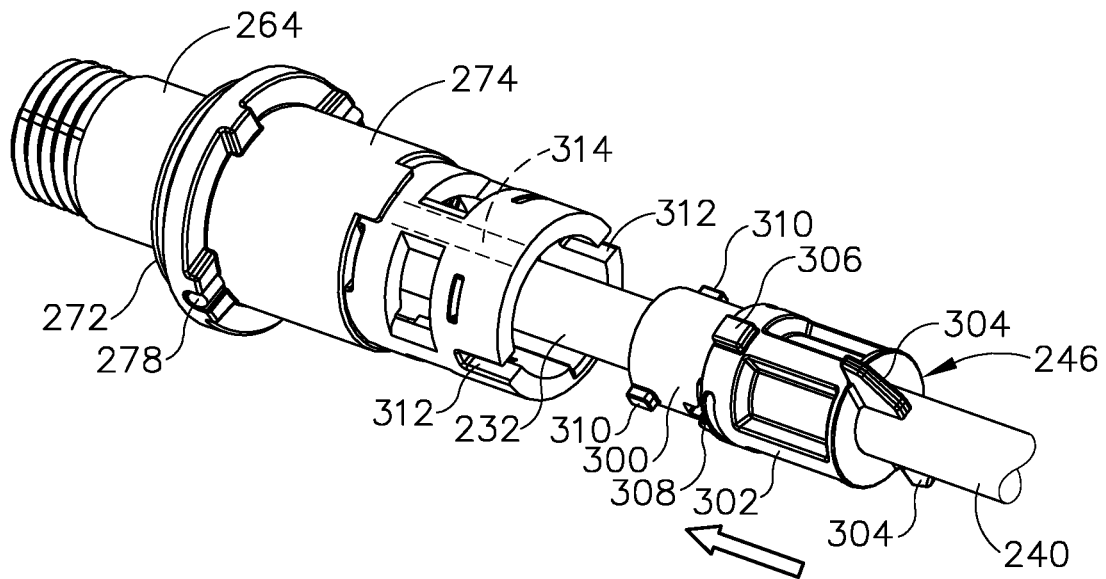
FIG. 22A depicts a perspective view of an alignment plug of the removable assembly and an inner alignment tube and an outer guide tube of the handle assembly, showing the alignment plug disassembled from the inner alignment tube and the outer guide tube.
Figure 22B:
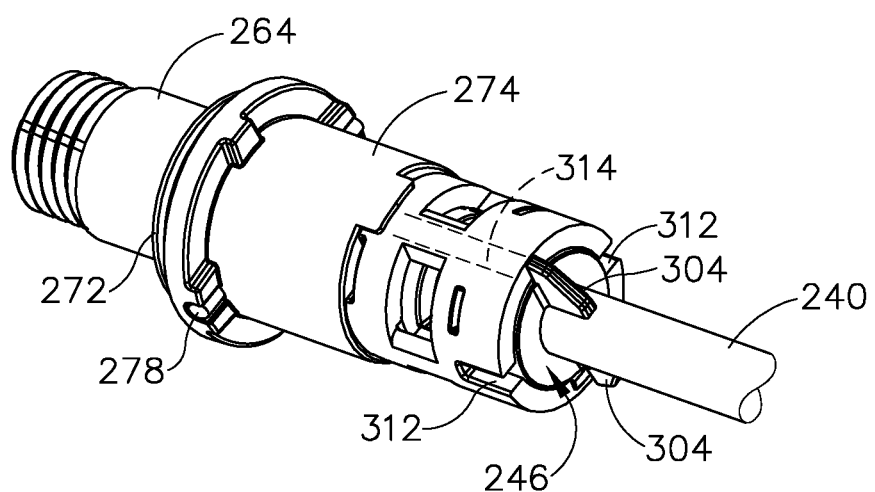
FIG. 22B depicts a perspective view of the components of FIG. 22A, showing the alignment plug assembled with the inner alignment tube and the outer guide tube, and in a first rotational position.

FIGS. 22A and 22B show passage of alignment plug (246) of removable clamp assembly (206) proximally over inner shaft tube (232) coupled to handle assembly (202), and subsequent proximal insertion of shaft alignment tube (264) into outer guide tube (274) and shaft alignment tube (264) of handle assembly (202). As shown in FIG. 22A, alignment plug (246) has a generally cylindrical proximal body portion (300) and a generally cylindrical distal body portion (302) of a larger diameter. A pair of opposed tab-like fins (304) are arranged at a distal end of distal plug body portion (302), and a key protrusion (306) is arranged at a proximal end of distal plug body portion (302) in the same plane as fins (304). A pair of opposed locking protrusions (308) extend radially from a distal end of proximal plug body portion (300) along a proximal face of distal plug body portion (302), and a pair of opposed lugs (310) are arranged at a proximal end of proximal plug body portion (300) in the same plane as lugs (310). In the present example, the plane in which lugs (310) and locking protrusions (308) are formed is angularly offset from the plane in which fins (304) and key protrusion (306) are formed by 90 degrees. As described below, this configuration enables alignment plug (246) to rotate clockwise 90 degrees relative to outer guide tube (274) and shaft alignment tube (264) between unlocked and locked positions.

As shown in FIG. 22A, outer guide tube (274) includes a generally cylindrical body having a distal end in which a pair of opposed fin slots (312) and a keyway (314) are formed. Fin slots (312) and keyway (314) each extend proximally, and are angularly offset from one another by 90 degrees in the present example. As shown in FIG. 22B, keyway (314) is configured to receive key protrusion (306) when alignment plug (246) is inserted proximally into outer guide tube (274), thereby orienting alignment plug (246) in an unlocked position relative to shaft alignment tube (264), as shown in FIG. 23A described below. In this unlocked position, distal faces of fins (304) abut a proximal face of outer guide tube (274) to thereby limit further proximal advancement of alignment plug (246) and outer shaft tube (240) relative to outer guide tube (274) and shaft alignment tube (264), thereby providing a clamp arm lockout feature.

FIG. 23A shows alignment plug (246) engaged with shaft alignment tube (264) in the unlocked position, with outer guide tube (274) being omitted from view. In this position, key protrusion (306) abuts a distal end of shaft alignment tube (264), and lugs (310) are received within respective axial lug slots (316) and are positioned in alignment with entry ends of respective circumferential lug slots (318) formed in a distal portion of shaft alignment tube (264). With alignment plug (246) in its unlocked position relative to shaft alignment tube (264) as shown in FIG. 23A, outer shaft tube (240) and clamp arm (244) are rotationally offset from inner shaft tube (232), waveguide (224), and ultrasonic blade (226) as shown in FIG. 23B. Specifically, clamp arm (244) is oriented such that clamp pad (250) extends generally perpendicularly relative to primary blade treatment surface (228) of ultrasonic blade (226). In this orientation, distal opening (234) of inner shaft tube (232) is rotationally offset from snap arm (248) of distal connector tube (242).

Figure 24A:
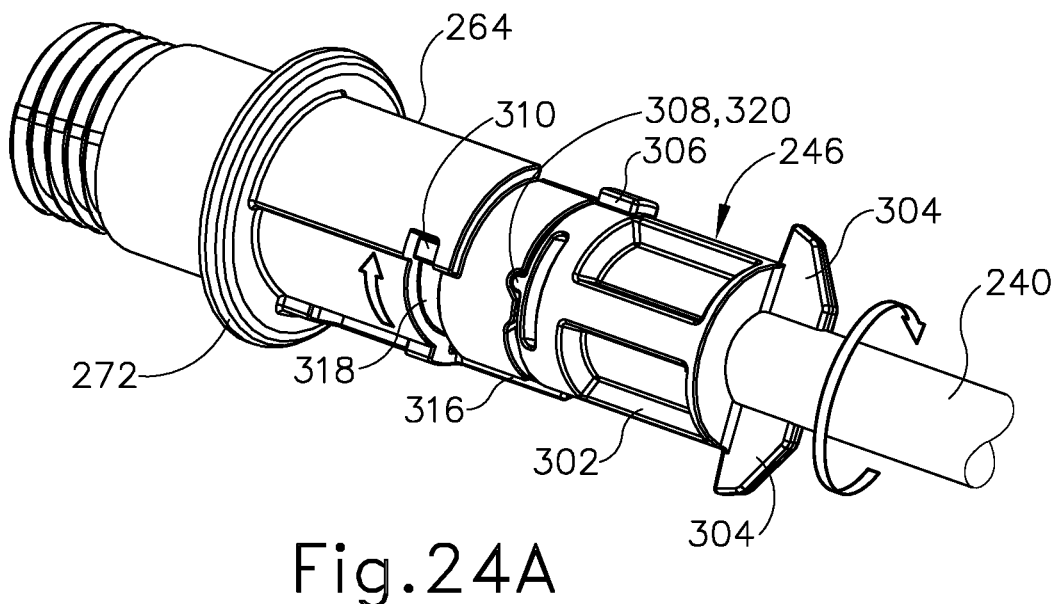
FIG. 24A depicts a perspective view of the alignment plug and the inner alignment tube of FIG. 23A, showing the alignment plug in a second rotational position relative to the inner alignment tube.
Figure 24B:
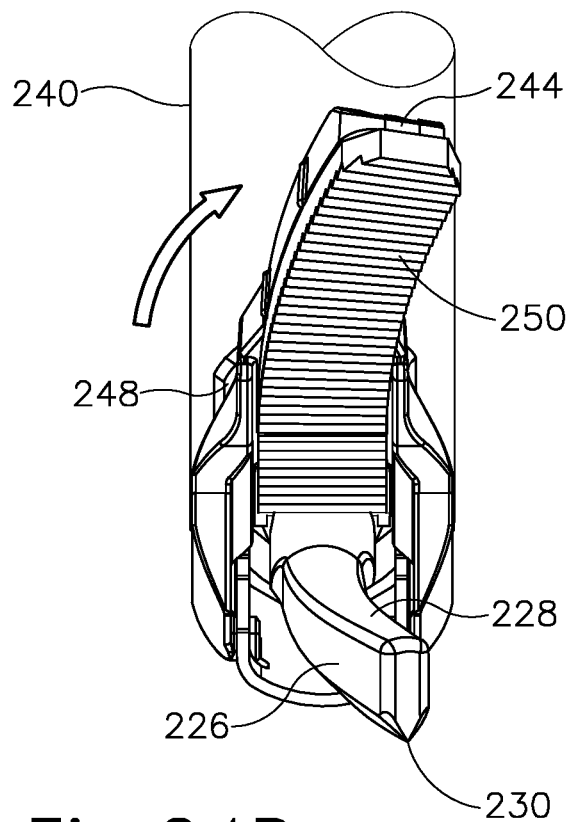
FIG. 24B depicts a perspective view of the end effector of FIG. 23B, showing the clamp arm in a second orientation corresponding to the second alignment plug position of FIG. 24A.

As shown in FIG. 24A, clamp assembly (206) is rotated clockwise 90 degrees relative to shaft alignment tube (264) to transition alignment plug (246) into a locked position. In the locked position, lugs (310) of alignment plug (246) are fully received within circumferential lug slots (318) of shaft alignment tube (264) in a bayonet style connection, and locking protrusions (308) of alignment plug (246) are received within respective notches (320) formed in a distal face of shaft alignment tube (264). As a result, alignment plug (246) is now secured axially and rotationally relative to shaft alignment tube (264). As shown in FIG. 24B, rotating alignment plug (246) into its locked position rotates outer shaft tube (240) and clamp arm (244) about waveguide (224) and inner shaft tube (232) such that clamp arm (244) is positioned in rotational alignment with primary blade treatment surface (228) of ultrasonic blade (226). Additionally, snap arm (248) of connector tube (242) is rotated into alignment with and lockingly engages distal opening (234) of inner shaft tube (232), thereby securing connector tube (242) axially and rotationally to inner shaft tube (232).

Figure 25A:
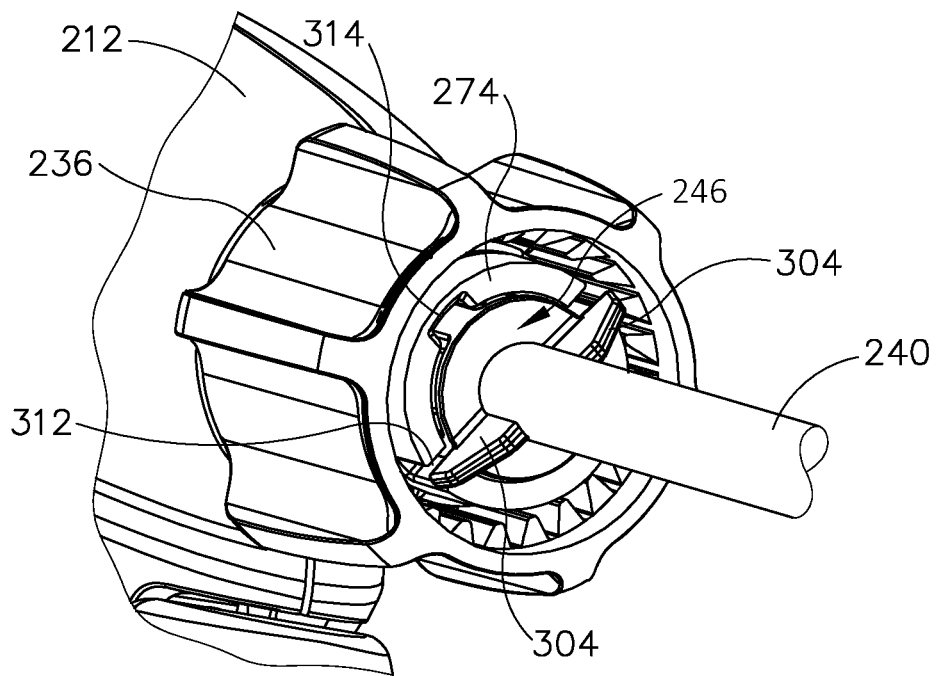
FIG. 25A depicts a front perspective view of the handle assembly of the ultrasonic surgical instrument of FIG. 16, showing the alignment plug in its second rotational position relative to the outer guide tube.
Figure 25B:
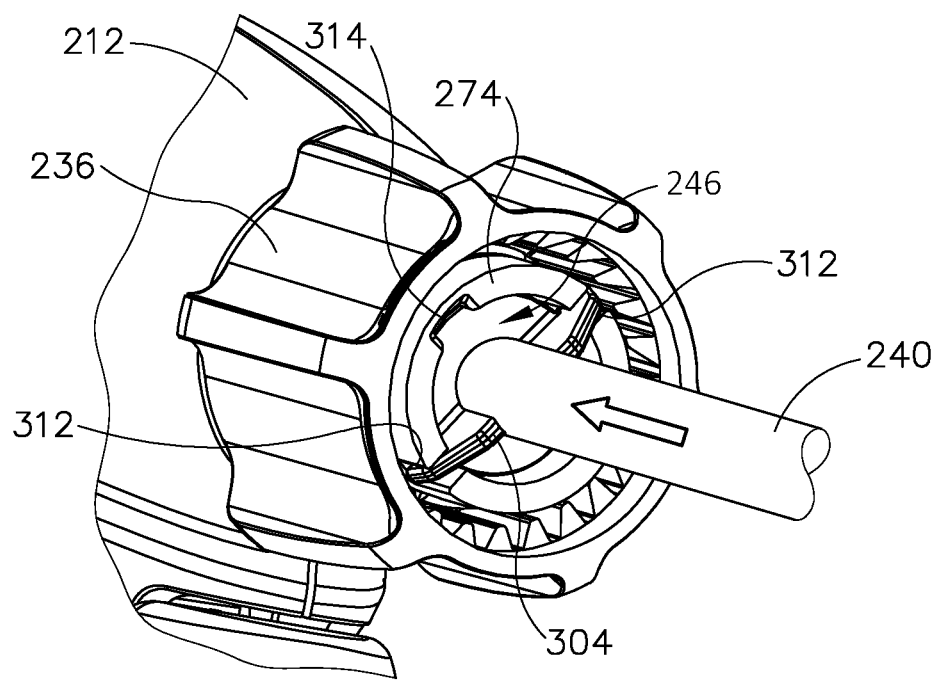
FIG. 25B depicts a front perspective view of the handle assembly of FIG. 25A, showing proximal actuation of the alignment plug and the outer shaft tube relative to the outer guide tube.

FIGS. 25A and 25B show front perspective views of ultrasonic surgical instrument (200) after alignment plug (246) has been rotated into its locked position relative to shaft alignment tube (264), as described above. In the locked position, fins (304) of alignment plug (246) align with fin slots (312) of outer guide tube (274). Accordingly, alignment plug (246) and outer shaft tube (240) are permitted to translate proximally with shaft alignment tube (264) relative to outer guide tube (274) when trigger (220) is squeezed toward pistol grip (214) to actuate clamp arm (244) relative to ultrasonic blade (226). As shown in FIG. 25B, fin slots (312) are formed with a proximal depth sufficient to enable outer shaft tube (240) to translate proximally enough to fully close clamp arm (244).

Following completion of a surgical procedure, removable clamp assembly (206) may be separated from handle assembly (202) by reversing the steps described above. Specifically, alignment plug (246) is rotated counter-clockwise 90 degrees relative to shaft alignment tube (264) and outer guide tube (274) so that lugs (310) disengage circumferential lug slots (318). Removable clamp assembly (206) may then be withdrawn distally from outer guide tube (274) and along inner shaft tube (232) until ultrasonic blade (226) is freed from clamp assembly (206).

D. Alternative Shaft Alignment Plug and Outer Guide Tube

Figure 26:
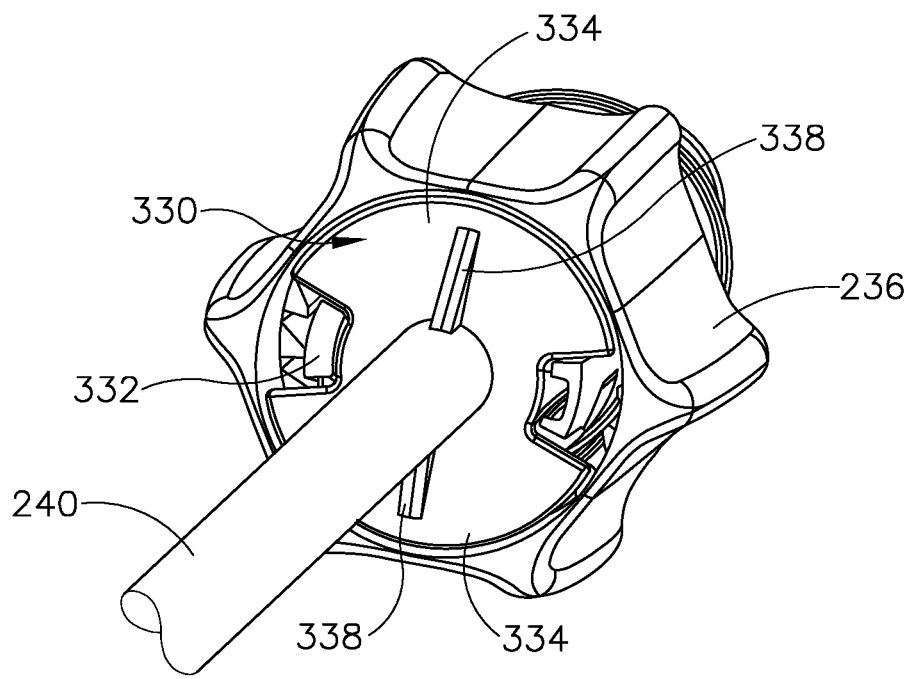
FIG. 26 depicts a front perspective view of another exemplary alignment plug and a corresponding outer guide tube.
Figure 27:
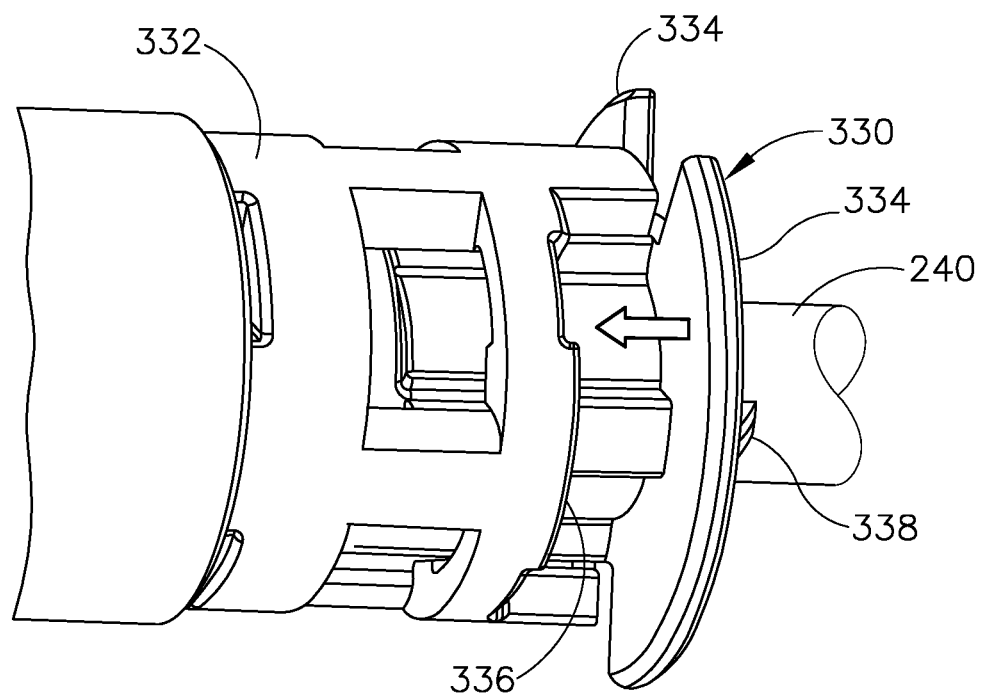
FIG. 27 depicts a side perspective view of the alignment plug and the outer guide tube of FIG. 26.

FIGS. 26 and 27 show another exemplary shaft alignment plug (330) and a corresponding outer guide tube (332) configured for use with handle assembly (202). Shaft alignment plug (330) and outer guide tube (332) are generally similar to alignment plug (246) and outer guide tube (274), except as otherwise described. In particular, shaft alignment plug (330) has a generally cylindrical body and a pair of opposed flanges (334) extending radially outwardly from a distal end of the body. Each flange (334) is generally planar in a direction transverse to the longitudinal axis of outer shaft tube (240), and is generally semi-circular in shape.

As shown in FIG. 27, outer guide tube (332) includes a pair of flange recesses (336) extending proximally and circumferentially in a distal end of outer guide tube (332). Recesses (336) are configured to receive flanges (334) when shaft alignment plug (330) is oriented in a locked position relative to shaft alignment tube (264) so as to position flanges (334) in rotational alignment with recesses (336). Accordingly, flanges (334) and recesses (336) cooperate to provide a clamp arm lockout feature similar to fins (304) and fin slots (312) described above, to ensure that clamp arm (244) cannot be actuated relative to ultrasonic blade (226) until they are positioned in rotational alignment with one another. Shaft alignment plug (330) may be rotated relative to outer guide tube (332) and shaft alignment tube (264)

between unlocked and locked positions via fins (338) projecting distally from flanges (334).

While the teachings herein are disclosed in connection with ultrasonic surgical instruments, it will be appreciated that they may also be employed in connection with surgical instruments configured to provide a combination of ultrasonic and radio frequency (RF) energies. Examples of such instruments and related methods and concepts are disclosed in U.S. Pat. No. 8,663,220, entitled "Ultrasonic Surgical Instruments," issued Mar. 4, 2014, the disclosure of which is incorporated by reference herein; U.S. Pub. No. 2015/0141981, entitled "Ultrasonic Surgical Instrument with Electrosurgical Feature," published May 21, 2015, issued as U.S. Pat. No. 11,141,213 on Oct. 12, 2021, the disclosure of which is incorporated by reference herein; and U.S. Pub. No. 2017/0000541, entitled "Surgical Instrument with User Adaptable Techniques," published Jan. 5, 2017, the disclosure of which is incorporated by reference herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An ultrasonic surgical instrument comprising: (a) a body; (b) an ultrasonic transducer configured to be supported by the body; (c) a shaft extending distally from the body and defining a shaft axis; (d) a waveguide configured to extend distally through the shaft; and (e) an end effector arranged at a distal end of the shaft, wherein the end effector comprises: (i) an ultrasonic blade coupled to a distal end of the waveguide and having a primary blade treatment surface configured to treat tissue, wherein the ultrasonic transducer is configured to drive the waveguide and the ultrasonic blade with ultrasonic energy, and (ii) a clamp arm coupled to the distal end of the shaft, wherein the clamp arm is configured to clamp tissue against the primary blade treatment surface, wherein the shaft and the waveguide are selectively rotatable relative to one another about the shaft axis through a predefined range of angular motion between an assembly state and an operational state, wherein in the assembly state the clamp arm and the primary blade treatment surface are rotationally offset from one another, wherein in the operational state the clamp arm and the primary blade treatment surface are rotationally aligned with one another.

EXAMPLE 2

The ultrasonic surgical instrument of Example 1, wherein the clamp arm is configured to confront the primary blade treatment surface when the surgical instrument is in the operational state.

EXAMPLE 3

The ultrasonic surgical instrument of any one or more of the preceding Examples, wherein the predefined range of angular motion comprises at least 90 degrees of angular motion.

EXAMPLE 4

The ultrasonic surgical instrument of any one or more of the preceding Examples, wherein the shaft comprises an outer shaft tube and an inner shaft tube configured to be received within the outer shaft tube, wherein the clamp arm is coupled to the outer shaft tube and the waveguide is disposed within the inner shaft tube, wherein the outer shaft tube and the inner shaft tube are rotatable relative to one another through the predefined range of angular motion.

EXAMPLE 5

The ultrasonic surgical instrument of Example 4, wherein the shaft further comprises a connector element configured to rotationally couple the outer shaft tube with the inner shaft tube when the surgical instrument is in the operational state.

EXAMPLE 6

The ultrasonic surgical instrument of any one or more of the preceding Examples, further comprising: (a) a first alignment member coupled to the body, and (b) a second alignment member coupled to waveguide, wherein the first and second alignment members are configured to engage one another to guide relative rotation between the shaft and the waveguide through the predefined range of angular motion.

EXAMPLE 7

The ultrasonic surgical instrument of Example 6, wherein the first alignment member includes one of a protrusion or a slot, wherein the second alignment member includes the other of a protrusion or a slot, wherein the protrusion is slidable within the slot.

EXAMPLE 8

The ultrasonic surgical instrument of any one or more of Examples 6 through 7, wherein the first alignment member comprises an alignment tube coupled to the body, wherein the waveguide is configured to extend distally through the alignment tube.

EXAMPLE 9

The ultrasonic surgical instrument of any one or more of Examples 7 through 8, wherein at least a portion of the slot extends angularly relative to the shaft axis and is configured to direct rotation of the waveguide relative to the shaft in response to distal movement of the protrusion through the slot.

EXAMPLE 10

The ultrasonic surgical instrument of Example 9, wherein the slot includes a first angular portion configured to direct rotation of the waveguide relative to the shaft in a first angular direction, and a second angular portion configured to direct rotation of the waveguide relative to the shaft in a second angular direction, wherein the second angular portion is arranged distally of the first angular portion.

EXAMPLE 11

The ultrasonic surgical instrument of any one or more of Examples 9 through 10, wherein the slot includes first and second camming surfaces configured to engage the protrusion to direct rotation of the waveguide relative to the shaft.

EXAMPLE 12

The ultrasonic surgical instrument of any one or more of Examples 6 through 8, wherein the first alignment member comprises an alignment tube coupled to the body, wherein the second alignment member comprises an alignment plug coupled to a proximal end of the shaft, wherein the alignment tube is configured to receive the alignment plug, wherein the alignment plug is configured to rotate relative to the alignment tube through the predefined range of angular motion for transitioning the instrument between the assembly state and the operational state.

EXAMPLE 13

The ultrasonic surgical instrument of Example 12, wherein the alignment plug is rotatable relative to the alignment tube between a first plug position in which the instrument is in the assembly state and the alignment plug is prevented from translating with the alignment tube relative to the body, and a second plug position in which the instrument is in the operational state and the alignment plug is permitted to translate with the alignment tube relative to the body to thereby actuate the clamp arm.

EXAMPLE 14

The ultrasonic surgical instrument of Example 13, wherein the alignment plug includes a lug, wherein the alignment tube includes a circumferentially extending slot configured to receive the lug, wherein the circumferentially extending slot has a first slot end that defines the first plug position and a second slot end that defines the second plug position.

EXAMPLE 15

The ultrasonic surgical instrument of any one or more of Examples 12 through 14, further comprising an outer guide tube coupled to the body, wherein the alignment tube is disposed within a first end of the outer guide tube, wherein the alignment plug is configured to be received within a second end of the outer guide tube.

EXAMPLE 16

An ultrasonic surgical instrument comprising: (a) a body; (b) an ultrasonic transducer configured to be supported by the body; (c) a waveguide extending distally from the ultrasonic transducer and terminating at an ultrasonic blade, wherein the ultrasonic transducer is configured to drive the waveguide and the ultrasonic blade with ultrasonic energy; (d) a first shaft tube extending distally from the body and defining a shaft axis; (e) a first shaft alignment member coupled to the body; and (f) a removable assembly selectively coupleable with the body, wherein the removable assembly comprises: (i) a second shaft tube configured to extend longitudinally with the first shaft tube when the removable assembly is coupled with the body, and (ii) a second shaft alignment member coupled to the second shaft tube, wherein the first and second shaft alignment members are configured to engage one another and guide relative rotation between the first and second shaft tubes to thereby orient the first and second shaft tubes in rotational alignment with one another when the removable assembly is coupled to the body.

EXAMPLE 17

The ultrasonic surgical instrument of Example 16, wherein one of the first or second shaft alignment members includes a protrusion, wherein the other of the first or second shaft alignment members includes a slot configured to receive the protrusion, wherein the slot is configured to guide the protrusion along a path that extends circumferentially about the shaft axis.

EXAMPLE 18

The ultrasonic surgical instrument of any or more of Examples 16 through 17, wherein the first shaft alignment member comprises a tube, wherein the tube is configured to rotate relative to the body about the shaft axis.

EXAMPLE 19

An ultrasonic surgical instrument comprising: (a) a body; (b) a shaft tube extending distally from the body; and (c) a removeable assembly selectively coupleable with the body, wherein the removable assembly comprises: (i) an ultrasonic transducer, and (ii) a waveguide extending distally from the ultrasonic transducer and terminating at an ultrasonic blade, wherein the waveguide is configured to be received within the shaft tube, wherein the ultrasonic transducer is configured to drive the waveguide and the ultrasonic blade with ultrasonic energy, wherein the waveguide and the ultrasonic blade are configured to rotate relative to the shaft tube through a predefined range of angular motion in response to longitudinal movement of the removable assembly relative to the body.

EXAMPLE 20

The ultrasonic surgical instrument of Example 19, further comprising: (a) a first alignment member coupled to the body, and (b) a second alignment member coupled to the removable assembly, wherein the first and second alignment members are configured to engage one another to guide rotation of the waveguide and the ultrasonic blade relative to the shaft tube.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic surgical instrument comprising:
   (a) a body;
   (b) a first shaft tube extending distally from the body and defining a shaft axis;
   (c) an ultrasonic blade having a primary blade treatment surface configured to treat tissue;
   (d) a removable clamp assembly selectively coupleable with the body, wherein the removable clamp assembly comprises:
      (i) a second shaft tube configured to extend longitudinally with the first shaft tube when the removable clamp assembly is coupled with the body, and
      (ii) a clamp arm coupled to a distal end of the second shaft tube, wherein the clamp arm is configured to clamp tissue against the primary blade treatment surface;
   (e) an alignment plug coupled to a proximal end of the second shaft tube; and
   (f) an alignment tube coupled to the body, wherein the alignment tube is configured to receive the alignment plug,
   wherein the first and second shaft tubes are selectively rotatable relative to one another about the shaft axis through a predefined range of angular motion between an assembly state and an operational state, wherein in the assembly state the clamp arm and the primary blade treatment surface are rotationally offset from one another, wherein in the operational state the clamp arm and the primary blade treatment surface are rotationally aligned with one another,
   wherein the alignment plug is configured to rotate relative to the alignment tube through the predefined range of angular motion between a first plug position in the assembly state and the alignment plug is prevented from translating with the alignment tube relative to the body, and a second plug position in the operational state and the alignment plug is permitted to translate with the alignment tube relative to the body to thereby actuate the clamp arm.

2. The ultrasonic surgical instrument of claim 1, wherein the clamp arm is configured to confront the primary blade treatment surface when in the operational state.

3. The ultrasonic surgical instrument of claim 1, wherein the predefined range of angular motion comprises at least 90 degrees of angular motion.

4. The ultrasonic surgical instrument of claim 1, wherein the alignment tube includes at least one slot, wherein the alignment plug includes at least one protrusion, wherein the at least one protrusion is slidable within the at least one slot.

5. The ultrasonic surgical instrument of claim 4, wherein the at least one protrusion includes a lug, wherein the at least one slot includes a circumferentially extending slot configured to receive the lug, wherein the circumferentially extending slot has a first slot end that defines the first plug position and a second slot end that defines the second plug position.

6. The ultrasonic surgical instrument of claim 1, further comprising an outer guide tube coupled to the body, wherein the alignment tube is disposed within a first end of the outer guide tube, wherein the alignment plug is configured to be received within a second end of the outer guide tube.

7. The ultrasonic surgical instrument of claim 6, wherein the alignment plug is prevented from translating proximally relative to the outer guide tube when the alignment plug is in the first plug position, wherein the alignment plug is permitted to translate proximally relative to the outer guide tube when the alignment plug is in the second plug position.

8. The ultrasonic surgical instrument of claim 7, wherein the outer guide tube includes a proximal face, wherein the alignment plug includes a body portion and at least one abutment member extending radially outwardly from the body portion, wherein the at least one abutment member of the alignment plug is configured to abut the proximal face of the outer guide tube when the alignment plug is in the first plug position to thereby prevent the alignment plug from translating proximally relative to the outer guide tube.

9. The ultrasonic surgical instrument of claim 8, wherein the outer guide tube includes at least one recess, wherein the at least one abutment member of the alignment plug is configured to angularly align with the at least one recess of the outer guide tube when the alignment plug is in the second plug position to thereby permit the alignment plug to translate proximally relative to the outer guide tube.

10. The ultrasonic surgical instrument of claim 9, wherein the alignment plug includes a key protrusion angularly aligned with the at least one abutment member.

11. The ultrasonic surgical instrument of claim 10, wherein the outer guide tube includes a keyway angularly offset from the at least one recess, wherein the keyway is configured to receive the key protrusion when the alignment plug is in the first plug position.

12. The ultrasonic surgical instrument of claim 8, wherein the at least one abutment member includes a pair of diametrically opposed abutment members.

13. The ultrasonic surgical instrument of claim 8, wherein the at least one abutment member includes at least one of a fin or a flange.

14. The ultrasonic surgical instrument of claim 1, further comprising:
   (a) an ultrasonic transducer configured to be supported by the body; and
   (b) a waveguide extending distally from the ultrasonic transducer and terminating at the ultrasonic blade, wherein the ultrasonic transducer is configured to drive the waveguide and the ultrasonic blade with ultrasonic energy.

15. The ultrasonic surgical instrument of claim 14, wherein the waveguide is configured to extend distally through the alignment tube.

16. A surgical instrument comprising:
   (a) a body;
   (b) a first shaft tube extending distally from the body and defining a shaft axis;
   (c) an alignment tube coupled to the body; and
   (d) a removable clamp assembly selectively coupleable with the body, wherein the removable clamp assembly comprises:
      (i) a second shaft tube configured to extend longitudinally with the first shaft tube when the removable clamp assembly is coupled with the body, and
      (ii) an alignment plug coupled to the second shaft tube,
      wherein the alignment tube and the alignment plug are configured to engage one another and guide relative rotation between the first and second shaft tubes to thereby orient the first and second shaft tubes in rotational alignment with one another when the removable clamp assembly is coupled to the body.

17. The surgical instrument of claim 16, wherein the alignment plug includes a protrusion, wherein the alignment tube includes a slot configured to receive the protrusion, wherein the slot is configured to guide the protrusion along a path that extends circumferentially about the shaft axis.

18. The surgical instrument of claim 16, wherein the alignment tube is configured to rotate relative to the body about the shaft axis.

19. An ultrasonic surgical instrument comprising:
(a) a body;
(b) an ultrasonic transducer configured to be supported by the body;
(c) a shaft extending distally from the body and defining a shaft axis;
(d) a waveguide configured to extend distally through the shaft;
(e) an end effector arranged at a distal end of the shaft, wherein the end effector comprises:
(i) an ultrasonic blade coupled to a distal end of the waveguide and having a primary blade treatment surface configured to treat tissue, wherein the ultrasonic transducer is configured to drive the waveguide and the ultrasonic blade with ultrasonic energy, and
(ii) a clamp arm coupled to the distal end of the shaft, wherein the clamp arm is configured to clamp tissue against the primary blade treatment surface,
(f) a first alignment member coupled to the body; and
(g) a second alignment member coupled to the shaft,
wherein the shaft and the waveguide are selectively rotatable relative to one another about the shaft axis through a predefined range of angular motion between an assembly state and an operational state, wherein in the assembly state the clamp arm and the primary blade treatment surface are rotationally offset from one another, wherein in the operational state the clamp arm and the primary blade treatment surface are rotationally aligned with one another,
wherein the first and second alignment members are configured to engage one another to guide relative rotation between the shaft and the waveguide through the predefined range of angular motion,
wherein the first alignment member comprises an alignment tube coupled to the body, wherein the second alignment member comprises an alignment plug coupled to a proximal end of the shaft, wherein the alignment tube is configured to receive the alignment plug, wherein the alignment plug is configured to rotate relative to the alignment tube through the predefined range of angular motion for transitioning between the assembly state and the operational state,
wherein the alignment plug is rotatable relative to the alignment tube between a first plug position in the assembly state and the alignment plug is prevented from translating with the alignment tube relative to the body, and a second plug position in the operational state and the alignment plug is permitted to translate with the alignment tube relative to the body to thereby actuate the clamp arm.

20. The ultrasonic surgical instrument of claim 19, wherein the alignment plug includes a lug, wherein the alignment tube includes a circumferentially extending slot configured to receive the lug, wherein the circumferentially extending slot has a first slot end that defines the first plug position and a second slot end that defines the second plug position.

* * * * *